United States Patent [19]
Shen et al.

[11] Patent Number: 5,768,407
[45] Date of Patent: *Jun. 16, 1998

[54] METHOD AND SYSTEM FOR CLASSIFYING AGGLUTINATION REACTIONS

[75] Inventors: Jian Shen, Somerset; Mykola Yaremko, Livingston; Rosemary Chachowski, Manville, all of N.J.; Josef Atzler, Hallein, Austria; Thierry Dupinet, Maennedorf, Switzerland; Daniel Kittrich, Praha, Czech Rep.; Hansjoerg Kunz, Zuerich, Switzerland; Karl Puchegger, Salzburg, Austria; Reiner Rohlfs, Frellassing, Germany

[73] Assignee: Ortho Diagnostic Systems, Inc., Raritan, N.J.

[*] Notice: The term of this patent shall not extend beyond the expiration date of Pat. No. 5,594,808.

[21] Appl. No.: 742,588

[22] Filed: Oct. 28, 1996

Related U.S. Application Data

[63] Continuation of Ser. No. 163,996, Dec. 8, 1993, Pat. No. 5,594,808, which is a continuation of Ser. No. 75,302, Jun. 11, 1993, abandoned.

[51] Int. Cl.⁶ .................................................. G06K 9/00
[52] U.S. Cl. ............................. 382/133; 382/134; 356/39; 422/73
[58] Field of Search .................................. 382/133, 134; 364/413.08, 555; 348/61; 73/64.41, 61.69; 356/39, 442, 436, 434; 422/73, 67; 436/43, 69, 165, 805

[56] References Cited

U.S. PATENT DOCUMENTS

| | | |
|---|---|---|
| 3,900,290 | 8/1975 | Hornstra . |
| 4,104,031 | 8/1978 | Robuchon-Merovak et al. . |
| 4,197,088 | 4/1980 | Meserol et al. . |
| 4,400,353 | 8/1983 | Meserol et al. . |
| 4,436,827 | 3/1984 | Tamagawa . |
| 4,443,408 | 4/1984 | Mintz . |
| 4,447,396 | 5/1984 | Kano . |
| 4,452,759 | 6/1984 | Takekawa . |
| 4,457,893 | 7/1984 | Takekawa . |
| 4,503,011 | 3/1985 | Hubeau . |
| 4,558,946 | 12/1985 | Galle et al. . |
| 4,563,430 | 1/1986 | Kano et al. . |
| 4,575,492 | 3/1986 | David et al. . |
| 4,580,895 | 4/1986 | Patel . |
| 4,683,120 | 7/1987 | Meserol et al. . |
| 4,727,033 | 2/1988 | Hijikata et al. . |
| 4,766,083 | 8/1988 | Miyashita et al. . |
| 4,767,600 | 8/1988 | Vicario . |
| 4,777,141 | 10/1988 | Calzi et al. . |
| 4,794,450 | 12/1988 | Saito et al. . |
| 4,806,015 | 2/1989 | Cottingham . |
| 4,826,319 | 5/1989 | Namba et al. . |
| 4,861,554 | 8/1989 | Sakuma . |
| 4,873,633 | 10/1989 | Mesei et al. . |
| 4,988,630 | 1/1991 | Chen et al. . |
| 5,169,601 | 12/1992 | Ohta et al. . |
| 5,192,692 | 3/1993 | Sakai et al. . |
| 5,225,350 | 7/1993 | Watanabe et al. . |
| 5,238,852 | 8/1993 | Sakai et al. . |
| 5,594,808 | 1/1997 | Shen et al. ............................ 382/133 |

Primary Examiner—Leo Boudreau
Assistant Examiner—Phuoc Tran
Attorney, Agent, or Firm—Dana M. Schmidt

[57] ABSTRACT

A method and system for analyzing a solution for an agglutination pattern. The method comprises the steps of producing an illuminated image of the solution on an array of pixels, and assigning to each pixel in the illuminated image, a data value representing the intensity of the illuminated image on the pixel. Those data values are then processed according to a predetermined program to determine if an agglutination pattern is present and, if so, to classify that pattern into one of a plurality of predefined classes. With the preferred processing procedure, the pixel array is separated into a plurality of zones, and the data values for the pixels in each zone are processed according to a respective predetermined procedure to determine values for a predefined set of variables. Then, those determined values are processed to determine whether an agglutination pattern is present in the solution, and if so, to classify that pattern into one of the predefined classes.

30 Claims, 18 Drawing Sheets

FIG.IIA 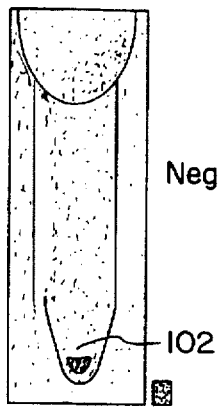
FIG.IIB 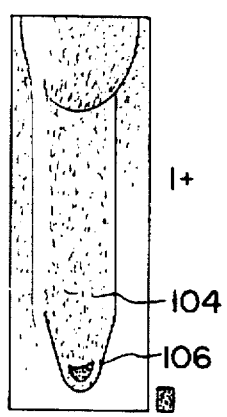
FIG.IIC 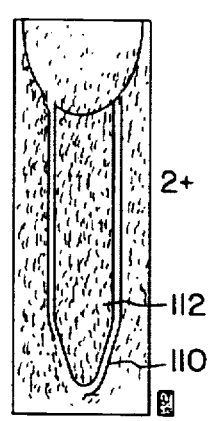
FIG.IID 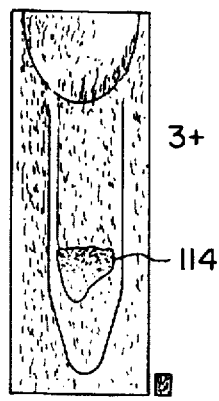
FIG.IIE 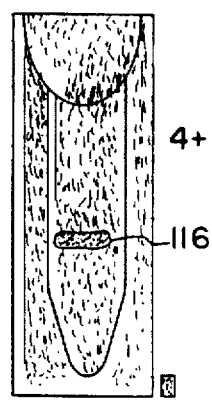

METHOD AND SYSTEM FOR CLASSIFYING AGGLUTINATION REACTIONS

This is a continuation of application Ser. No. 08/163,996, filed on Dec. 8, 1993, now U.S. Pat. No. 5,594,808, which is a continuation of application Ser. No. 08/075,302, filed on Jun. 11, 1993, now abandoned.

BACKGROUND OF THE INVENTION

This invention generally relates to a method and system for the detection and quantification of agglutinates formed in response to immunological agglutination reactions, and more particularly, to such a method and system employing automated image and data processing means to automatically detect and classify agglutination patterns.

Immunological agglutination reactions are used for identifying various kinds of blood types and for detecting various kinds of antibodies and antigens in blood samples and other aqueous solutions. In a conventional procedure, a sample of red blood cells is mixed with serum or plasma in test tubes or microplates, and the mixture may then be incubated and centrifuged. Various reactions either occur or do not occur depending on, for example, the blood type of the red blood cells or whether certain antibodies are present in the blood sample. Typically, these reactions manifest themselves as clumps of cells or particles with antigens and antibodies on their surfaces, referred to as agglutinates. Thus, the absence of any such clumps indicates that no reaction has occurred; and the presence of such clumps indicates that a reaction has occurred, with the size and amount of such clumps being a quantitative indicator of the level or concentration in the sample, or an indicator of the reaction strength, affinity of the complex for which the blood sample was tested.

Recently, a new agglutination test method—referred to as column agglutination technology, or CAT—has been developed. Column Agglutination Technology may be defined as the analysis of blood and blood products utilizing filtration as a means of separating agglutinated, precipitated, absorbed, or adsorbed particulate components from non-reactive components for immunoassay applications. In this method, gel or glass bead microparticles are contained within a small column, referred to as a microcolumn. A reagent such as anti-IgG is dispensed in a diluent in the microcolumn and test red blood cells are placed in a reaction chamber above the column. The column, which is typically one of a multitude of columns formed in a transparent cassette, is centrifuged. The centrifuging accelerates the reaction, if any, between the reagent and the blood cells, and also urges the cells toward the bottom of the column. The glass beads or gel in the microcolumn act as a filter, however, and resist or impede downward movement of the particles in the column. As a result, the nature and distribution of the particles in the microcolumn after centrifuging provides a visual indication of whether any agglutination reaction occurred in the microcolumn, and if so, of the strength of that reaction.

In particular, if no agglutination reaction occurs, then all or virtually all of the red blood cells in the microcolumn pass downward, during centrifuging, to the bottom of the column and form a pellet at that bottom. If there is a very strong reaction between the reagent and the red blood cells, virtually all of the red blood cells agglutinate, and large agglutinates form at the top of the microcolumn, above the gel or glass beads contained therein. The gel or glass beads prevent the agglutinates from passing, during centrifuging, to the bottom of the column, so that after centrifuging the agglutinates remain above the gel or beads.

If there is a reaction between the reagent and the blood cells, but this reaction is not as strong as the above-described very strong reaction, then some but not all of the red blood cells agglutinate. The percentage of red blood cells that agglutinate and the size of the agglutinated particles both vary directly with the strength of the reaction. During centrifuging, the unreacted blood cells pass to the bottom of the column, and the distance that the agglutinated particles pass downward through the column depends on the size and number of those particles. Hence, the size of the pellet of red blood cells at the bottom of the microcolumn, and the extent to which the agglutinates penetrate into the gel or glass beads in the microcolumn, are both inversely related to the strength of the reaction between the reagent and the red blood cells.

With this CAT, after the desired processing steps have been performed, the microcolumn is observed, or read, by a human operator, who then classifies the reaction between the reagent and the red blood cells. Conventionally, the reaction is classified as either negative or positive; and if positive, the reaction is then further classified into one of four classes depending on the strength of the reaction. A highly skilled operator is needed to properly read and classify the reaction.

SUMMARY OF THE INVENTION

An object of this invention is to automatically analyze aqueous solutions for agglutination patterns.

Another object of the present invention is to automatically read and classify agglutination reactions between red blood cell antigens and antibodies.

A further object of this invention is to produce an image of a blood sample and to analyze that image using high speed image and data processing equipment to determine if the blood sample contains an agglutination pattern and, if so, to classify that pattern.

A still another object of the present invention is to provide a system and method for automatically reading and classifying agglutination reactions that occur in a column having a microfilter that produces different agglutination patterns depending on the strength of that reaction.

Another object of this invention is to provide a system for reading and classifying blood samples that may be used alone or as part of an integrated, fully automated blood bank system.

A further object of this invention is to provide an accurate, high speed method and system for automatically reading and classifying red blood cell agglutination reactions.

These and other objectives are attained with a method and system for analyzing a solution for an agglutination pattern. The method comprises the steps of producing an illuminated image of the solution on an array of pixels, and assigning to each pixel in the illuminated image, a data value representing the intensity of the illuminated image on the pixel. These data values are then processed according to a predetermined program to determine if an agglutination pattern is present and, if so, to classify that pattern into one of a plurality of predefined classes. With the preferred processing procedure, the pixel array is separated into a plurality of zones, and the data values for the pixels in each zone are processed according to a respective predetermined procedure to determine values for a predefined set of variables. Then, those determined values are processed to determined whether an agglutination pattern is present in the solution, and if so, to classify that pattern into one of the predefined classes.

With the preferred embodiment of the invention disclosed herein in detail, the solutions are contained in a column having glass microbeads. The image processing program searches the location of the column in the source image on the pixel array; and after the column is located, the program generates a window to cover the column where the red cells are located. The program then selects three reference regions from inside and outside the column and measures the intensity or gray levels in these regions, and these measured gray levels are used to determine certain threshold values that are subsequently used in the processing program.

The cell pellet is extracted by applying global threshold values in a V-shaped, lower portion of the column, and parameters related to the shape of the cell pellet are also calculated. The program then generates a fixed mask to cover the bead area in the column.

For the feature calculation, the bead column is divided into five different zones. The region on top of the bead column is defined as the positive zone, the region at the bottom of the column is defined as the negative zone, and the area between the positive and negative zones is separated into three intermediate zones. The red cells located in the positive zones are extracted using a threshold method, and the red cell agglutinates located in the intermediate zones are extracted using a morphological filter. In addition, the balance of the red cells between the left and right sides of the column is determined. For each column, the above parameters are preferably calculated for both front and back side images of the column, and the two calculated values for each parameter are combined. The agglutination reaction is then classified on the basis of these combined features.

Further benefits and advantages of the invention will become apparent from a consideration of the following detailed description given with reference to the accompanying drawings, which specify and show preferred embodiments of the invention.

BRIEF DESCRIPTION OF THE DRAWINGS

FIGS. 11A–11E show different agglutination patterns that may be produced in a column of the cassette shown in FIGS. 3–5.

DETAILED DESCRIPTION OF THE PREFERRED EMBODIMENTS

Figure 1:
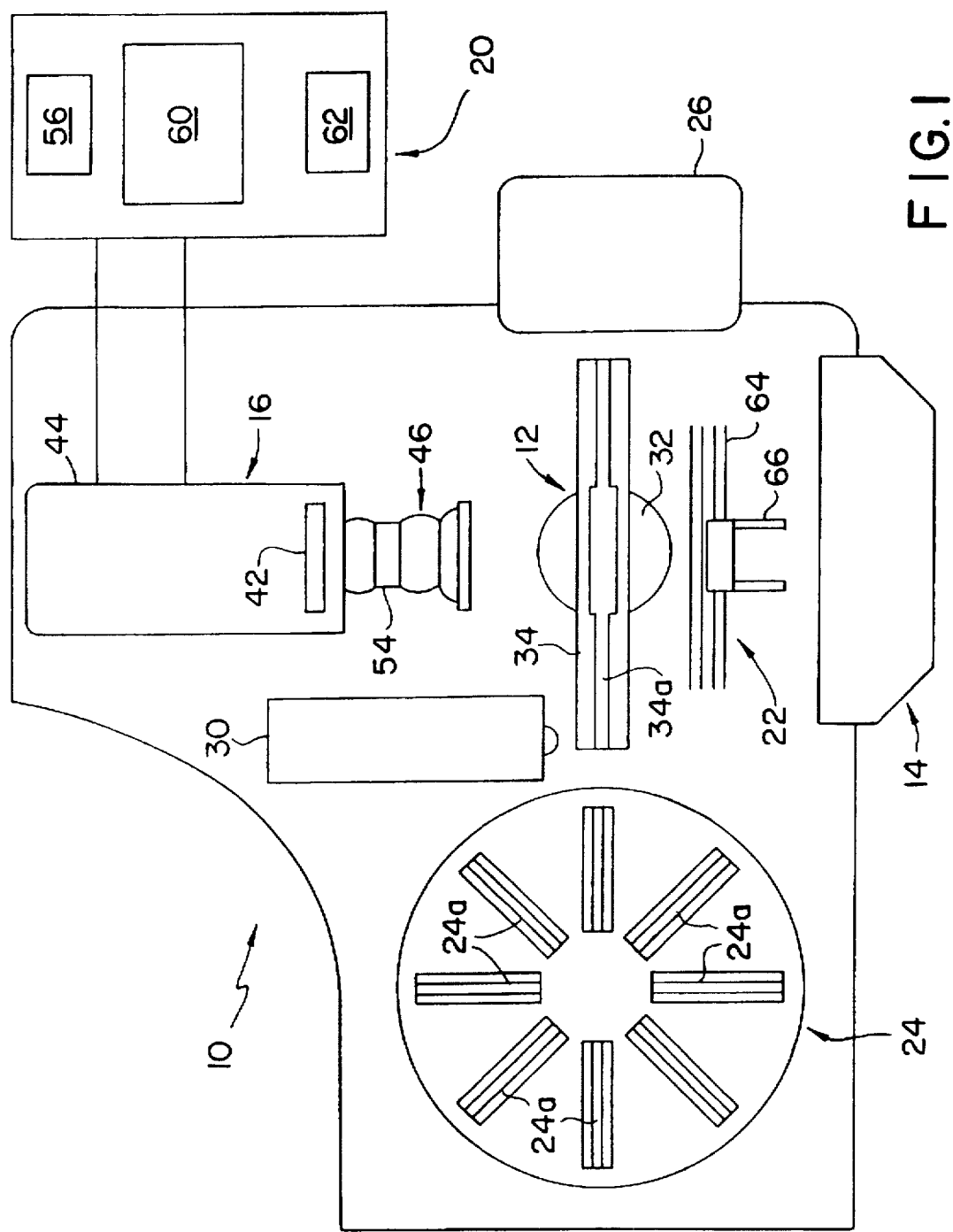
FIG. 1 is a schematic diagram of an automated blood analysis system embodying the present invention.
Figure 2:
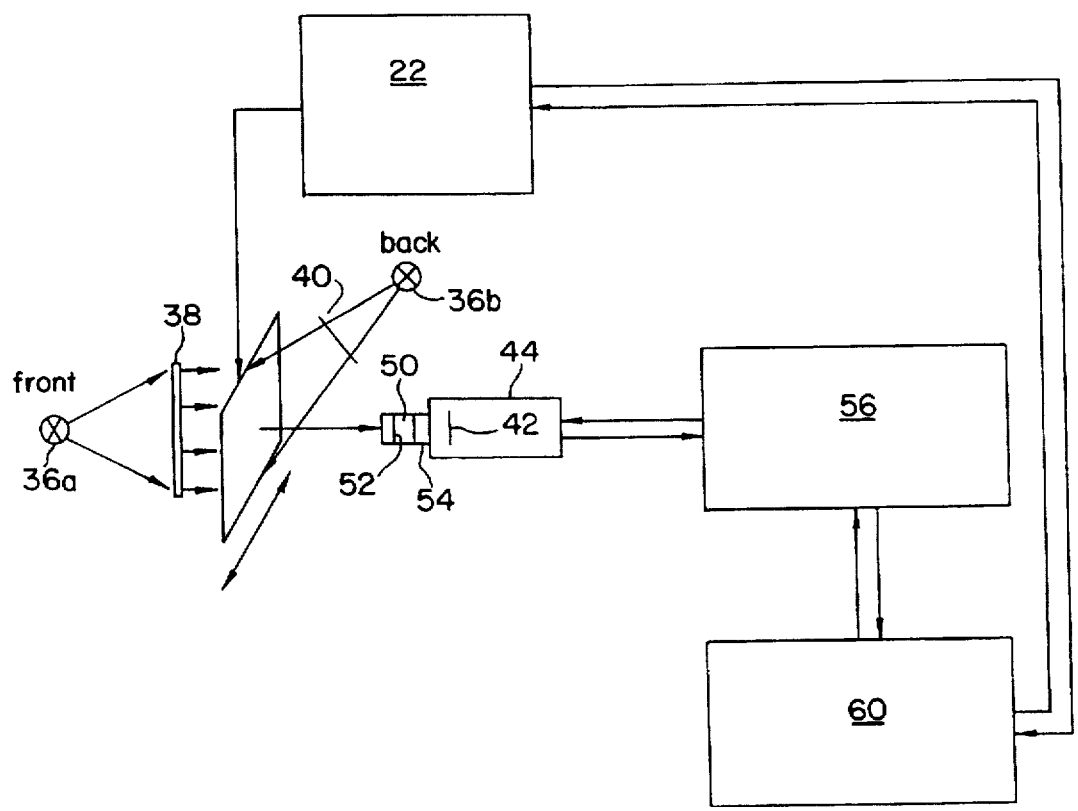
FIG. 2 is a block diagram illustrating several components of the system of FIG. 1.

FIGS. 1 and 2 illustrate automated optical reading system 10, generally, comprising holding means 12, illumination means 14, imaging subsystem 16, and processing subsystem 20; and preferably system 10 further includes transport subsystem 22, storage means 24, waste receptacle 26, and bar code reader 30. With the embodiment of system 10 shown in FIG. 1, holding means 12 includes base 32 and frame 34; and illumination means includes a pair of fluorescence lights 36a and 36b, diffuser 38, and neutral density filter 40. Imaging subsystem 16 includes pixel array 42, housing 44, and lens assembly 46; and this lens assembly, in turn, includes lens 50, filter 52, and lens housing 54. Also, the preferred processing subsystem 20 includes preprocessor 56, main processor 60, and input means such as keyboard 62; and the preferred transport subsystem 22 shown in FIG. 1 includes support means 64 and mover 66.

Generally, holding means 12 is provided to hold a test sample for analysis, and illumination means 14 is provided to produce an illuminated image of the test sample on imaging subsystem 16. Subsystem 16 generates a set of signals representing the illuminated image formed thereon and then transmits those signals to processing subsystem 20. The processing subsystem receives those signals from subsystem 16 and processes those signals according to a predetermined program to determine whether an agglutination pattern is present in a test sample being analyzed and, if so, to classify that pattern in one of a plurality of predefined classes.

The preferred embodiment of system 10 described herein in detail is particularly well suited for analyzing blood samples, and these samples are often referred to as solutions. It should be noted that the present invention may be embodied in systems that analyze other materials, including other aqueous solutions such as urine. It is not necessary, though, that the material being analyzed be a liquid or a fluid; and, thus, the term "solution" as used herein is used in the general sense as any mixture of liquid, gaseous, or solid substances.

In addition, the test samples analyzed in system 10 are preferably held within containers, and a large variety of types and sizes of containers may be used with system 10. However, the preferred embodiment of system 10 described herein in detail is particularly well suited for use with containers of the type shown at 80 in FIGS. 3, 4, and 5. These containers, referred to as cassettes, are made from a transparent, integrally molded plastic material. A multitude of cavities or wells 82, referred to as columns or microcolumns, are formed in the cassettes and extend downward from the top edge of the cassette, and, for example, the cassette shown in FIGS. 3–5 contains six such microcolumns.

A multitude of very small, transparent glass beads, having diameters on the order of magnitude of 10 to 100 micrometers, are deposited in and form a filter in the lower portion of each microcolumn. Alternately, the lower portion of each microcolumn may be provided with a suitable gel that functions in the same general way as the microbeads. Reagents may be pre-dispensed in the columns of the cassette; and after the columns of the cassette are provided with the desired materials, a foil 84 is typically secured on the top edge of the cassette to cover and close the tops of columns 82.

When any particular cassette 80 is used, one, some, or all of the microcolumns 82 in the cassette may be used. Moreover, each cassette may be used with blood samples from one or more individuals. In each microcolumn that is used, a sample of red blood cells and one or more reagents that react with known agents are pipetted into the microcolumn to test that blood sample for the presence of that one or more agents. The cassette may be incubated and is then centrifuged. If an agent, for which the blood sample is being tested, is present in the microcolumn, the agent reacts with the red blood cells to form agglutinates; and the number, size, and distribution of the agglutinates in the microcolumn is an indication of the strength of that reaction.

With reference again to FIG. 1, frame 34 of holding means 12 forms an elongated channel 34a for holding a test sample such as cassette 80; and preferably, as shown in FIG. 1, the longitudinal ends of the channel 34a are open to facilitate or to allow sliding movement of the test sample into, through, and then from channel 34a. Also, frame 34 is preferably rotatably mounted on base 32 for pivotal or rotary movement about a central vertical axis, and a motor is connected to frame 34 to pivot or rotate the frame about that axis.

Illumination means 14, which preferably comprises a pair of fluorescence lamps 36a and 36b, directs light through the test sample held in frame 34 and onto imaging subsystem 16, and specifically onto pixel array 42, which then generates a series of signals representing the test sample. More particularly, pixel array 42 is disposed inside a camera housing 44, and the pixel array is preferably comprised of a multitude of light sensors each of which is capable of generating a respective one electric current having a magnitude proportional to or representing the intensity of light incident on that sensor. Preferably, these light sensors, or pixels, are arranged in a uniform grid of a given number of uniformly spaced rows and columns.

With reference again to FIG. 2, lens 50 and filter 52 are located forward of pixel array 42 and are coaxially aligned with each other and with the pixel array, and lens 50 is positioned so that the pixel array is at the back focal plane of this lens. Preferably, lens 50 and filter 52 are mounted inside housing 54, which in turn is mounted on the front end of camera 44.

As will be understood by those of ordinary skill in the art, any suitable light source 14, lens 50, filter 52, and camera 44 may be used in system 10. For example, in an embodiment of system 10 that has been actually reduced to practice, camera 44 is a Sony XC-75CE video camera, and the pixel array or sensoring element in this camera is a charged coupled device (CCD) comprising a matrix of pixels in a rectangular array, 752 pixels by 582 pixels. The distance between the camera and the cassette held in frame 34 was adjusted so that each image on the pixel array contains two columns 82 of the cassette, and the width of each column in the image is about 152 pixels.

A Componon microlens manufactured by Schneider Corporation was set at an F stop of F/4.0 and attached on the camera via an adaptor. Between the lens and the CCD element was fixed a band pass filter with a center wavelength of 550 nm and a band width of 40 nm. This filter enhances the image of the red cells and improves the signal to noise ratio, and the filter was selected on the basis of a spectrophotometer measurement, which indicates that red blood cells have increased absorption of light in the corresponding wavelength range.

Figure 6A:
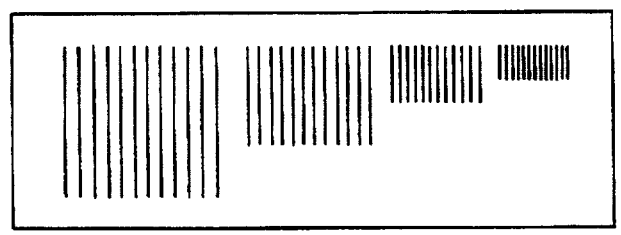
FIG. 6A shows a glass pattern that may be used to focus the camera of the system shown in FIG. 1.
Figure 6B:
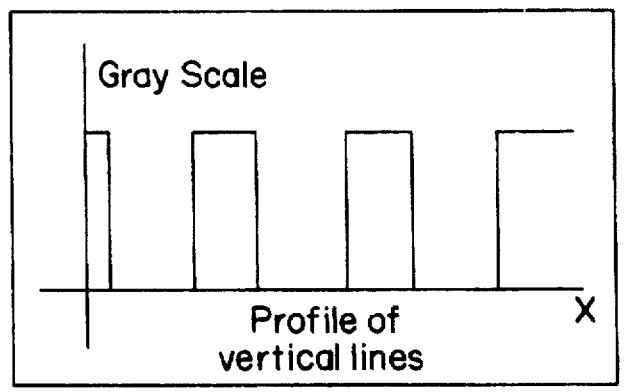
FIGS. 6B and 6C show two pattern signals that may be produced on the camera using the glass pattern of FIG. 6A, depending on whether the camera is in focus or out of focus.
Figure 6C:
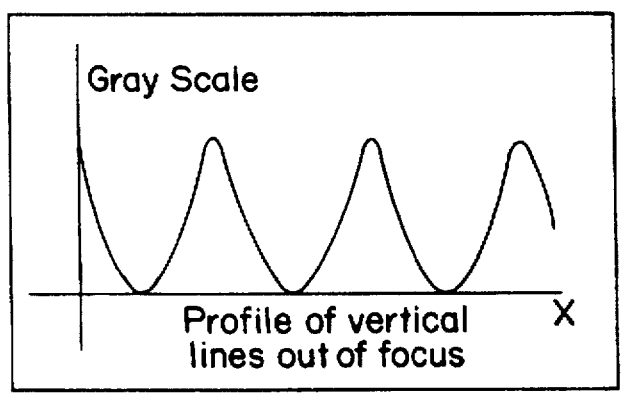

The camera 44 was focused using a piece of glass printed with special patterns. These patterns are dark vertical lines with different sizes and widths as shown in FIG. 6A. If the camera is in focus, the signal profile of the pattern image is a square wave, as shown in FIG. 6B. If the camera is out of focus, the signal profile looses the sharp edge, as shown in FIG. 6C. The pattern signal is derived, and the optimal focus is reached when the maximum derivative value is obtained.

In this embodiment of system 10 that has been actually reduced to practice, light source 14 includes two constant fluorescence tubes 36a and 36b (manufactured by Phillips, PL-S, 7-W), a diffuser 38, and a neutral density filter 40. As particularly shown in FIG. 2, one fluorescence tube 36a was mounted in the front of the cassette, and the other fluorescence tube was located upward and rearward of the cassette. The neutral density filter 40 is located below the fluorescence tube 36b, and this filter is used to reduce the amount of light transmitted to the cassette from tube 36b. The diffuser 38 is located parallel to and approximately 1.0 mm forward of cassette.

Figure 7:
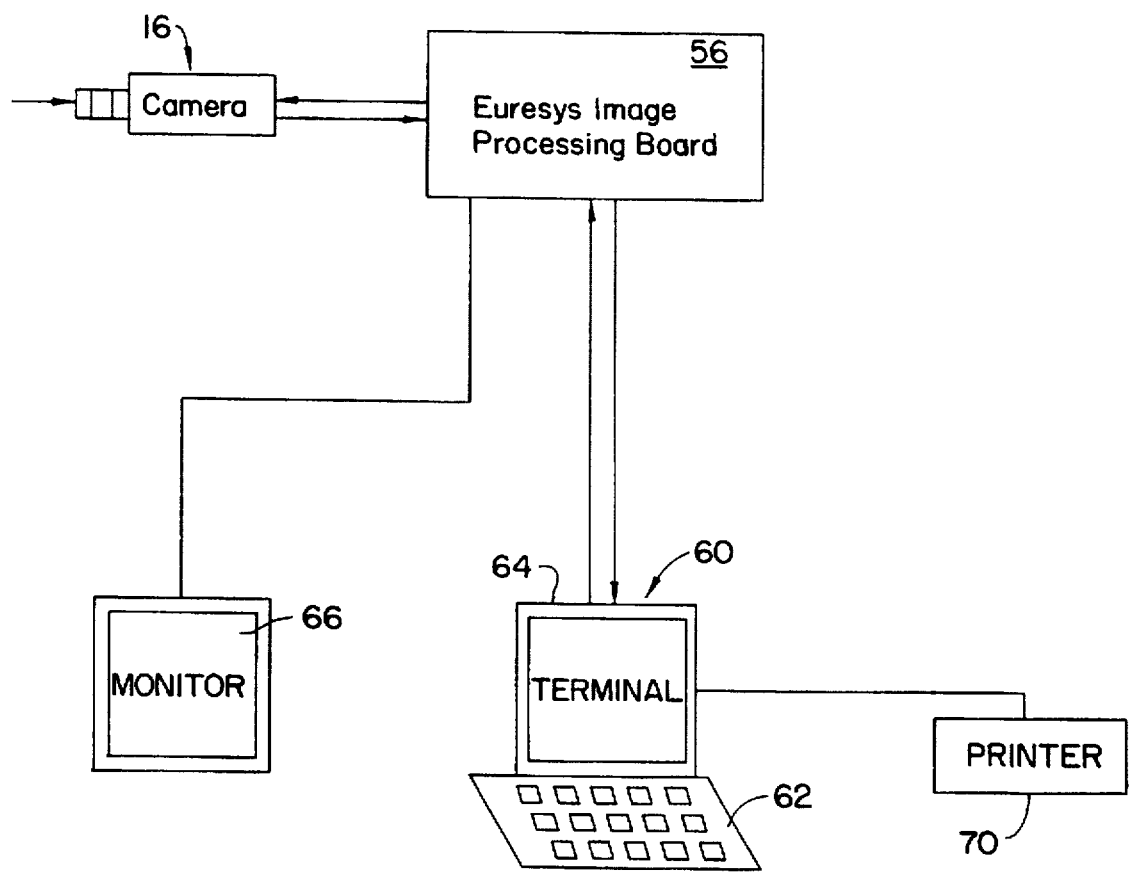
FIG. 7 is a more detailed drawing of the processing subsystem of the analysis system of FIG. 1.

FIG. 7 is a block diagram illustrating processing subsystem 20 in greater detail. In this subsystem, the electric signals from the pixel array in camera 44 are conducted to preprocessor 56, which may be, for example, an image processing board made by Euresys S. A. of Belgium. This image processor then converts the electric signal from each pixel of array 42 into a respective one digital data value and stores that data value at a memory location having an address associated with the address of the pixel that generated the electric signal. The electric signals being transmitted to image processor 56 may be identified in any suitable way with the specific pixel that generated the signal. For instance, the signals from the pixels of array 42 may be transmitted to the image processor in a given, timed sequence, and a clock signal may be transmitted to the image processor from the camera to identify the start, or selected intervals, of that sequence. Alternately, each signal transmitted to the image processor may be provided with a header or another data tag identifying the particular pixel that generated the signal.

Figure 8:
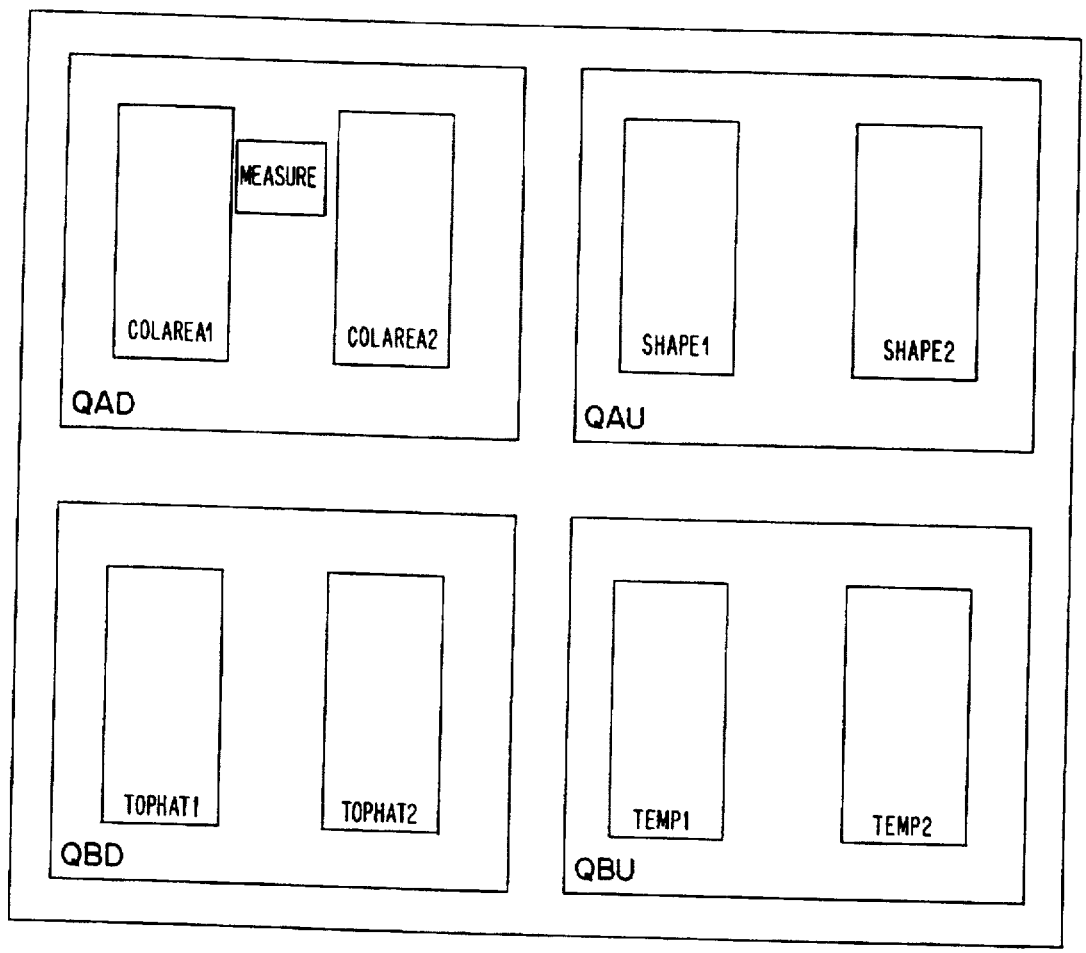
FIG. 8 schematically illustrates the memory board of the image processes of the processing subsystem.

The Euresys image processing board consists of 1 MB memory. As shown in FIG. 8, the memory is divided into four quads: QAU, QAD, QBU, and QBD. Each quad contains a frame of 512×512 pixels. The source image data, S, is located in one quad QAD, and Quad QAU contains two fixed masks used for covering the two columns in the later image processing. Quad QBD is used for a procedure referred to as top-hat processing, discussed below, and Quad QBD is used for temporary operation.

The data values stored in image processor 56 are available to main processor 60, which is connected to the image processor to obtain data values from and to transmit data values to that image processor. As explained in greater detail below, processor 60 is programmed to process and to analyze the data values stored in the image processor to identify the agglutination pattern, if any, in the test sample being analyzed.

Preferably, main processor is, or is a component of, a personal computer also having keyboard 62 and terminal 64. Keyboard 62 is connected to processor 60 to allow operator input thereto, and terminal 64 is used to display visually data or messages being input into the processor. In addition, monitor 66 may be connected to processor 56 to produce video images from the data value stored in the processor or in image processor 56. For example, the S data values may be transmitted to monitor 66 to produce thereon an image of the real image produced on pixel array 42. Other sets of data values may be transmitted to the monitor to produce refined or processes images of the real image. Printer 68 may be connected to processor 60 to provide a visual, permanent record of selected data values transmitted to the printer from the processor.

As will be understood by those of ordinary skill in the art, subsystem 20 may be provided with other or additional input or output devices to allow an operator or analyst to interact with processors 56 and 60. Also, the individual components of subsystem 20 are conventional and well-known by those of ordinary skill in the art. For example, monitor 66 may be a high resolution color monitor; and, as discussed above, processor 60 may be a personal computer, and image processor 56 may be an image processing board made by Euresys S. A. of Belgium.

With reference again to FIG. 1, storage means 24 is located adjacent holding means 12 and is provided for holding a multitude of test samples, and preferably indexing means such as a stepper motor is provided for moving the storage means through a series of positions to align each of the test samples held therein with the holding means. The storage means 24 shown in FIG. 1 is particularly designed for holding cassettes 80, and the storage means forms a multitude of channels or slots 24a for holding those cassettes. The indexing means moves this storage means 24 so as to align each of the channels 24a with the elongated channel 34a of frame 34, allowing the cassettes to be slid from the storage means and into that frame.

With the preferred embodiment of system 10 shown in FIG. 1, storage means 24 comprises a rotatable carousel including a rotatable base and a multitude of compartments. Each compartment forms a respective one of the channels or slots 24a, and each of these slots extends along a radius of the carousel. Further, the indexing means may comprise a stepper motor, and each time the motor is actuated, the motor moves the carousel so as to align one of the slots 24a with channel 34a of frame 34. This stepper motor may be operated, for example, to rotate carousel to align one slot 24a at a time with channel 34a, in a clockwise or counterclockwise sequence around the carousel. Alternatively, the stepper motor may be provided with a programmed, or programmable, controller that operates the stepper motor to align slots 24a with channel 34a according to that program and in an order that may depend on a multitude of variable factors.

Waste receptacle 26 is provided for receiving the test samples from holding means 12 after the desired imaging has been completed. For example, the waste receptacle may be a container located below and adjacent the output end of channel 34a of frame 34, and positioned so that the test samples that are slid out from channel 34a fall into receptacle 26 under the force of gravity.

Transport subsystem 22 is preferably provided to move test samples, particularly cassettes 80, into and then from holding means 12, specifically frame channel 34a. More particularly, with reference to FIGS. 1, 9, and 10, support means 64 supports mover 66 for sliding movement between carousel 24 and waste receptacle 26 and over frame 34. In use, mover 66 is positioned over the carousel, and as the carousel rotates to align a cassette with frame slot 34a, that cassette is moved into engagement with the mover. The mover then slides the cassette from carousel 24, into frame 34 and into a position directly forward of pixel array 42. After the desired imaging of the test sample is completed, the mover 66 is operated to slide the test sample through the output end of channel 34a and into waste receptacle 26. Alternatively, depending on the results of the analysis of the test sample, that test sample may be moved back into carousel 24, or to another location where the test sample may be stored, for example, for further tests or for analysis by an operator.

Figure 9:
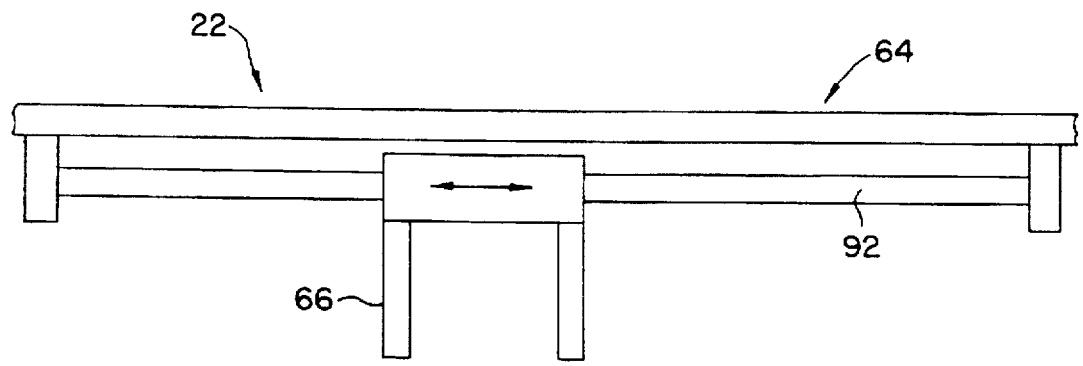
FIG. 9 is a front view of the transport subsystem of the analysis system shown in FIG. 1.
Figure 10:
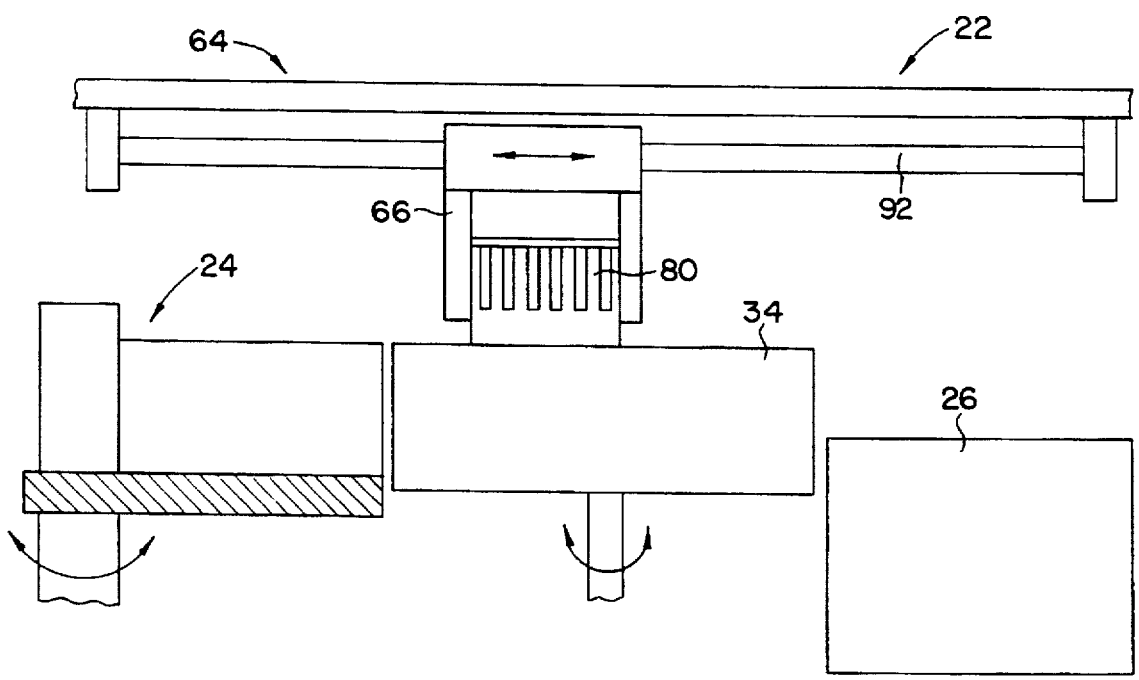
FIG. 10 illustrates the transport subsystem in the analysis system.

With particular reference to FIGS. 9 and 10, support means 64 includes a horizontal bar 92; and this bar extends from a position directly over carousel 24 to a position directly over waste receptacle 26, and bar 92 is supported in any suitable manner. Mover 66, in turn, is supported by and is mounted on bar 92 for sliding movement therealong, and a suitable motor or motors (not shown) are provided to operate the mover. Mover 66 may be operated in response to electric signals received from sensors or timers or both, to move the test sample in the desired manner. Alternatively, the mover may be controlled by a programmed, or programmable, processor that operates transport subsystem 22 in a predetermined manner and according to a multitude of variable factors.

Preferably, each cassette 80 is provided with a bar code 86 identifying selected data about the cassette, and bar code reader 30 is provided to read the bar code on each cassette and to transmit the data thereon to processor 60. For example, the bar code on the cassette may identify the cassette type, the date of manufacture of the cassette, and a recommended expiration date for the cassette. The bar code may include other data that identify the cassette manufacturer as well as the time and place of manufacture. As shown in FIG. 1, the code reader, which may be a standard bar code reader, is preferably located between storage rack 24 and frame 34 so that the reader scans the bar code on each cassette as the cassette is being transferred from the storage rack and into the frame 34. As an option, if the bar code 86 does not properly identify all the selected data, system 10 may be operated so that there is no processing of any image data from the cassette 80. For example, this may be done by not producing any image of the cassette on pixel array 42, or if an image is produced, by not processing that image.

In the operation of system 10, a multitude of test samples are placed in carousel 24, and the carousel is rotated to align a selected one of the slots 24a with channel 34a. Then, mover 66 slides the test sample in that selected carousel slot, into the desired position in frame 34, and illumination means 14 then directs a beam of light through the test sample and onto pixel array 42. Cassette 80 may include positioning marks 88 between the columns 82, or elsewhere on the cassette, to help align the cassette in frame 34; and system 10 may be operated so that, if the cassette does not have any such positioning marks, or if the marks are not properly aligned in frame 34, the cassette is rejected or there is no analysis or processing of the cassette.

Each pixel of array 42 generates a respective one electric current having a magnitude representing the intensity of the light incident on that pixel; and these output currents are converted to digital data values, referred to as gray values or as the S values, and stored in image processor 56. Preferably, frame 34 is then rotated 180°, and illumination means directs another light beam through the test sample to produce a further image of the test sample on the pixel array. Each pixel of array 42 generates another respective one electric current having a magnitude representing the intensity of the light of the second image that is incident on the pixel. These output currents are converted to a second set of digital data values, which are also stored in the image processor. These two images of the test sample that are produced on the pixel array are referred to as the front and back images, respectively.

Processing subsystem 20 then analyzes the images produced on the pixel array, in a manner discussed in detail below, to classify the particle patterns in the test sample, and on the basis of that classification, to classify the reaction between the reagent and the blood cells in the test sample. After the image processing is complete, mover 66 may be used to slide the test sample into waste receptacle 26. Alternatively, if processor 60 determines that the test sample should receive further analysis or, for some reason, should be specifically brought to the attention of a human operator, then the test sample may be carried, by mover 66, another mechanism, or an operator, to a separate holding area.

In the meantime, carousel 24 is rotated to align a second carousel slot with frame channel 34a; and once mover 66 is available, that mover may be used to move the test sample from that second carousel slot into the frame channel. The desired image or images of that second test sample are produced and then processed to classify the reaction between the blood cells and the reagents in the test sample.

The above procedure may be continuously repeated until stopped by an operator, or an automated controller may be provided to stop the procedure in accordance with a predetermined program. During the operation of system 10, new test samples may be placed in carousel 24 either by an operator or by a suitable mechanism.

System 10 is particularly well suited for use in an automated solution testing system or instrument. For example, a blood analysis system or instrument in which system 10 may be used, is disclosed in patent application No. , for "An Automated Blood Analysis System," filed herewith, the disclosure of which is herein incorporated by reference.

As previously mentioned, when the test sample is held in a column 82 of a cassette 80, the number, size, and distribution of particles in the column is an indication of whether an agglutination reaction occurred in that column and, if so, of the strength of the reaction. Conventionally, the reaction is classified as negative (if no reaction occurred) or as positive (if a reaction has occurred), and if positive, the reaction is further classified as a class +1, +2, +3, or +4 reaction depending on the strength of the reaction.

Figure 3:
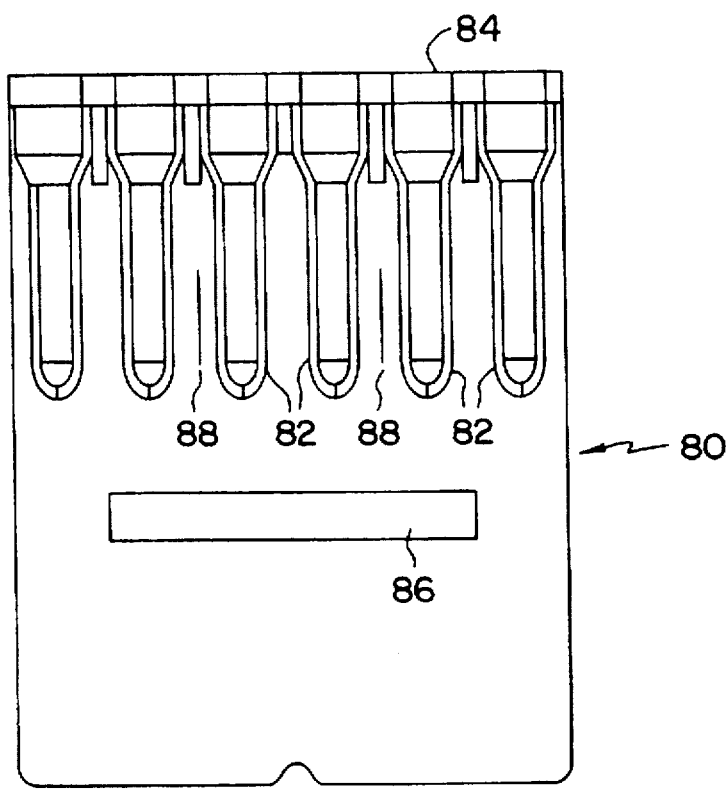
FIG. 3 is a front view of a solution cassette that may be used in the system of FIG. 1.
Figure 4:
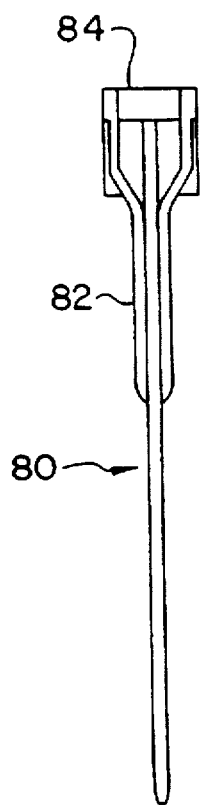
FIG. 4 is a side view of the cassette.
Figure 5:
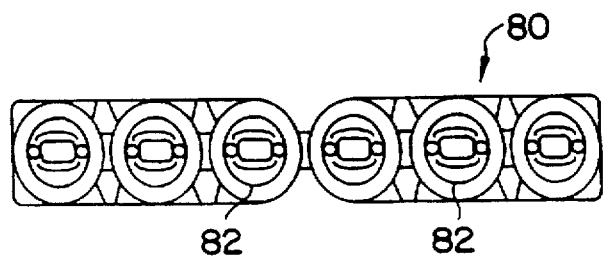
FIG. 5 is a top view of the cassette.

FIGS. 11A through 11E illustrate these five types of reactions—negative, class +1, class +2, class +3, and class +4, respectively—in a CAT using cassettes 80 of the type shown in FIGS. 3 and 4. With reference to FIG. 11A, in the case of a negative reaction, the red blood cells do not agglutinate and, during centrifuging, those cells pass to the bottom of the column and form a pellet 102 at that bottom. In a weak, or class +1, positive reaction, some of the blood cells agglutinate and form a relatively small number of small agglutinated particles 104; however, most of the red blood cells do not react. During centrifuging, agglutinated particles become distributed in the lower half of the microbead column, and the unreacted red blood cells pass to the bottom of the column and form a pellet 106 thereat that is slightly smaller than the pellet 102 formed in the case of a negative reaction.

In a class +2 reaction, which is slightly stronger than a class +1 reaction, a larger percentage of the red blood cells agglutinate and the agglutinated particles that form are larger; however, an appreciable number of the red blood cells still do not react. With reference to FIG. 11C, during centrifuging, the unreacted blood cells pass through the column bottom and form a small pellet 110, and larger agglutinate particles 112 become distributed throughout the length of the column of microbeads. In a class +3 reaction, most or virtually all of the red blood cells agglutinate and the agglutinated particles that form tend to be larger than those that form in a class +2 reaction. As shown in FIG. 11D, even after centrifuging, most of the agglutinated particles 114 remain in the upper half of the bead column. In a class +4 reaction, all, or virtually all, of the red blood cells agglutinate and form large agglutinates 116 at the top of the glass beads. These beads prevent the agglutinates from passing downward during centrifuging so that, after centrifuging, the agglutinates remain above the beads, as shown in FIG. 11E.

The reagent and the glass beads in column 82, as well as the body of cassette 80, are substantially transparent; however, the agglutinated particles and the red blood cells are only partially transparent. Hence, in the operation of system 10, when light is transmitted through column 82 and onto pixel array 42, the portion of the light that passes through the agglutinated particles and the red blood cells is incident on the array at a relatively low intensity, while the rest of the light passing through column 82 is incident on the array at a higher intensity. Accordingly, in the image of column 82 that is formed on pixel array 42, the agglutinated particles and the red blood cells appear as gray or shadow areas relative to the rest of the image.

Figure 12:
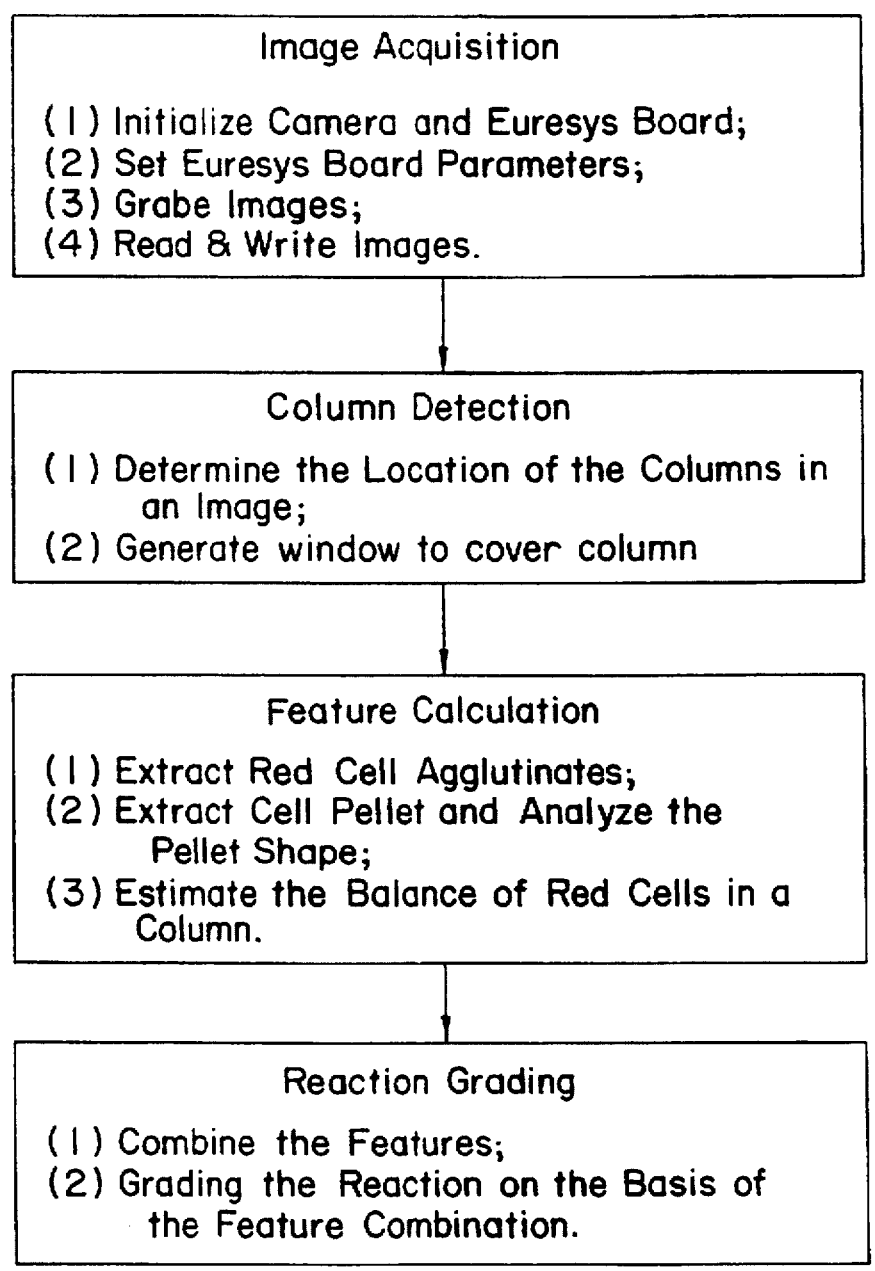
FIG. 12 generally outlines the preferred procedure for processing the image data produced in the system of FIG. 1.

With reference to FIG. 12, the preferred procedure for processing the image produced on pixel array includes four programs: (1) image acquisition, (2) column detection, (3) feature extraction, and (4) reaction classification. The image acquisition program relates to the management of and the interface between camera 44 and preprocessor 56, and the column detection program identifies the borders of the columns that appear on the pixel array. The feature extraction program extracts information related to the agglutination reactions from the source image and translates that information into quantitative data. The reaction classification program separates the reactions into different classes on the basis of the extracted features.

The first step in the image acquisition program is an initialization step. In this step, the video memory is cleared, several variables, discussed below, are set to associated values, and camera 44 is placed in checked mode. Then, after a cassette 80 is positioned in front of the camera by the transport subsystem 22, the image acquisition program sends a synchronization signal to the camera, and the camera shutter operates so that an image of the cassette is produced on pixel array 42. The image data values are then obtained by the image processing platform and converted into digitized signals that are stored in the image processor. To optimize the source image signals, the gain and offset of the electronic board is preferably adjusted with a gray scale so that the gray level of a black strip is zero, and the gray level of the glass beads is 170.

Figure 13:
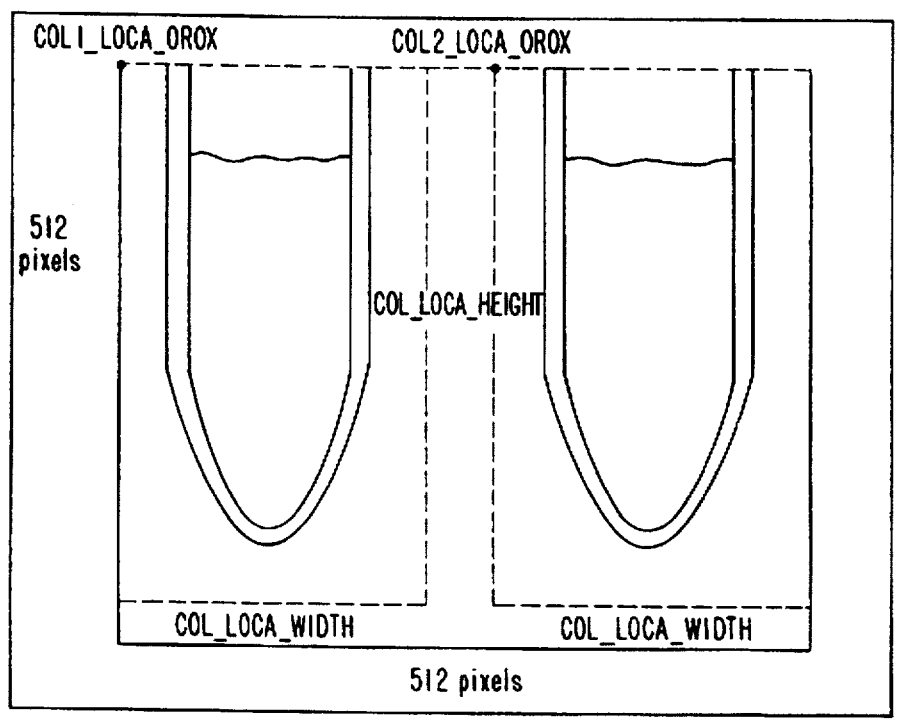
FIG. 13 illustrates one step in identifying the locations of the image of the columns in the pixel array of FIG. 1.

After the image acquisition program is completed, the column detection program begins. The first step in this program is to search for the positions of the two columns in the image frame, and in particular, to search for the left, right, and bottom edges of the two columns on the pixel array. This is done by using the fact that, due to the diffraction of light by those edges, those edges appear on the pixel array slightly darker than the immediately adjacent areas. More specifically, with reference to FIG. 13, the program creates two rectangular areas on the pixel array to cover the regions where the two columns are expected to be located. The size of each area may be, for example, 220 by 500 pixels, and the position of each rectangle is determined by preset x and y coordinates of the upper left corner of the rectangle. These parameters are listed below:

| Name | Value | Description |
| --- | --- | --- |
| COL_LOCA_WIDTH | 220 | width of the frame |
| COL_LOCA_HEIGHT | 500 | height of the frame |
| COL1_LOCA_ORGX | 0 | x-coordinate of the left column |
| COL2_JOCA_ORGX | 292 | x-coordinate of the right column |

The Y-coordinates for the upper left corners of both areas are zero.

Figure 14:
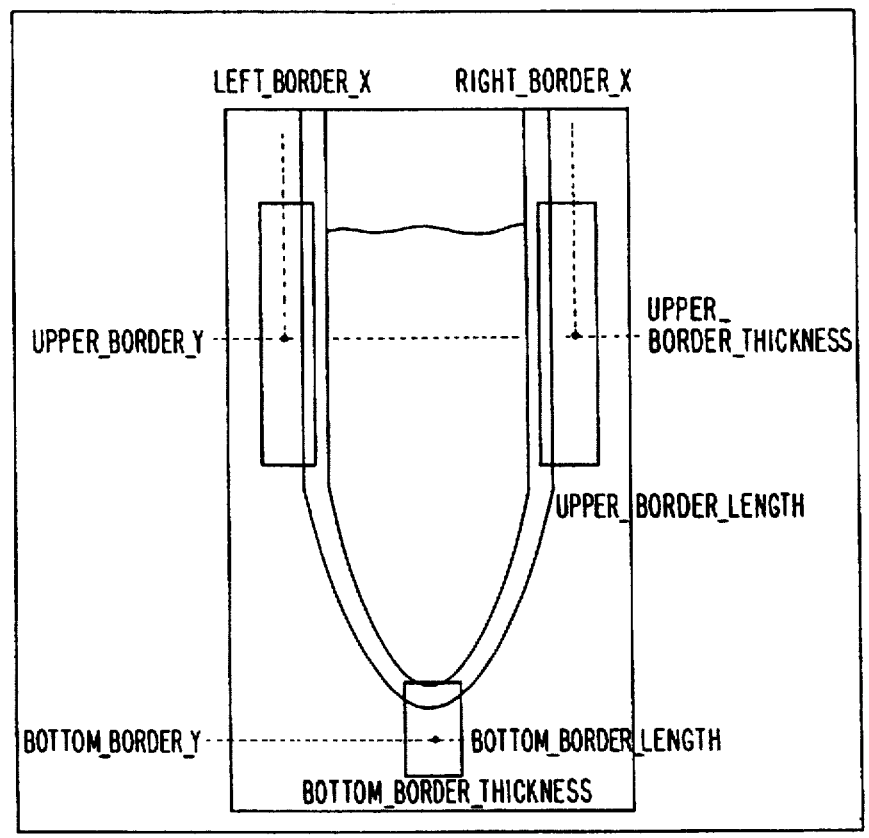
FIG. 14 illustrates a step in identifying the edges of a column image.

To detect the left and right edges of the columns, the program then generates three small areas within each rectangular window, as shown in FIG. 14. The positions of these areas are defined by the following coordinates:

| Name | Value | Description |
| --- | --- | --- |
| UPPER_BORDER_LENGTH | 25 | segment length |
| UPPER_BORDER_THICKNESS | 199 | projection thickness |
| UPPER_BORDER_Y | 160 | y-coordinate of the middle of the area |
| LEFT_BORDER_X | 30 | x-coordinate of the middle of the left area |
| RIGHT_BORDER_X | 190 | x-coordinate of the middle of the right area |
| BOTTOM_BORDER_LENGTH | 45 | segment: length |
| BOTTOM_BORDER_THICKNESS | 19 | projection thickness |
| BOTTOM_BORDER_Y | 435 | y-coordinate of the middle of the area |

The two left and right symmetric areas are used to detect the left and right side borders of the column. The gray values in the blocks are projected into two one-dimension vectors. At each point on each vector, a projected value is obtained by adding the gray values at all pixels in the corresponding vertical line through that point. The length of the vector is defined by the UPPER_BORDER_LENGTH. These values are then derived and the maximal derivative is obtained. This maximal derivative corresponds to the maximal variation of the gray scale, and on the basis of its location, the edge of the column is determined. The edge of the column is on the vertical line segment extending through the pixel having this maximal derivative.

It should be noted that it is not necessary to practice the present invention in its broadest sense that the left and right edges of each column be found independent of each other. For instance, as an alternative, one of those edges may be found; and then the other edge of the column may be considered as being on the vertical line segment parallel to and spaced a preset distance from that found edge, either to the left or to the right thereof depending on whether the initially found edge is on the right or left edge, respectively, of the column.

Once the left and right borders of each column are found, the column detection program then searches for the bottom border of the column. This search also utilized the fact that, due to the diffraction of light by that edge, that edge appears slightly darker on the pixel array than the immediately adjacent areas. More specifically, once the x-coordinates of the two side borders are found, the centerline of the column is determined and used as a reference to locate the third, bottom rectangular area shown in FIG. 14. This area, in turn, is used to locate the bottom edge of the column by means of a procedure analogous to the procedures used to detect the left and right edges of the column. In particular, the gray values in the block are projected onto a one-dimensional vertical vector. At each point on the vector, a projected value is obtained by adding the gray values of all the pixels in the corresponding horizontal line through that point. These values are then derived and the maximal derivative is obtained. This maximal derivative corresponds to the maximal variation of the gray scale, and the bottom edge of the column is considered to be on the horizontal line segment extending through the pixel having this maximal variation.

Figure 16:
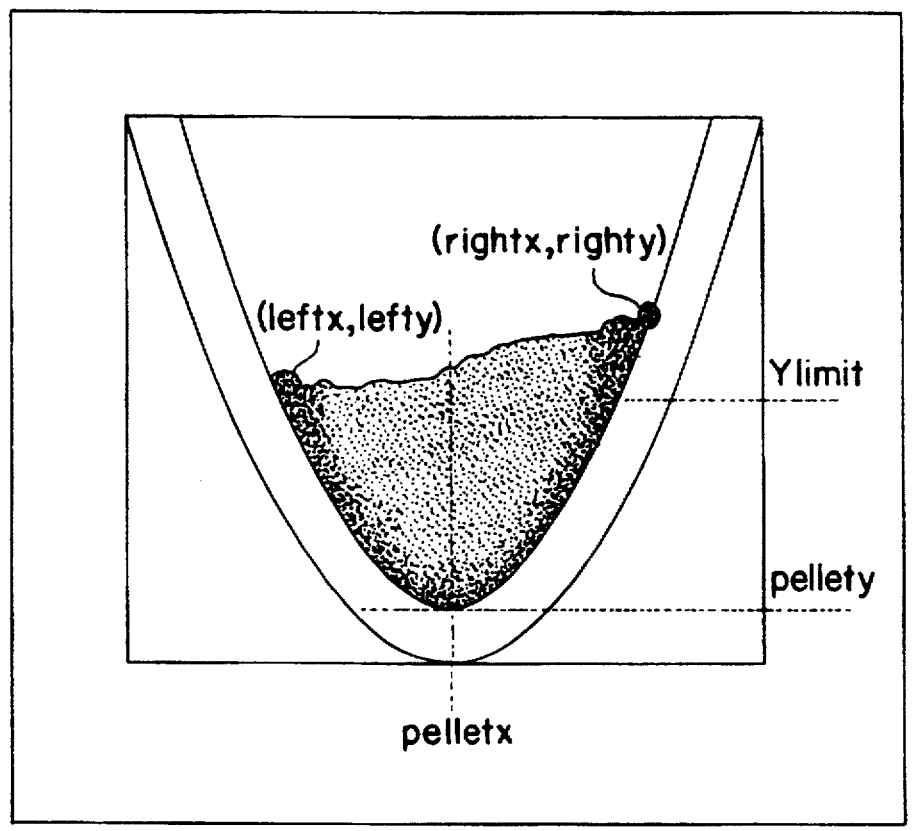
FIG. 16 shows a pellet of red blood cells at the bottom of a column.

Once the center line and the bottom point of each column are determined, a smaller window is superimposed over each column. This window which is shown in FIG. 16, has the same width as a column; and by matching the center and the bottom of the window with those of the column detected above, the window is fitted onto the column. Thus, the location of each column is fully determined.

Figure 15:
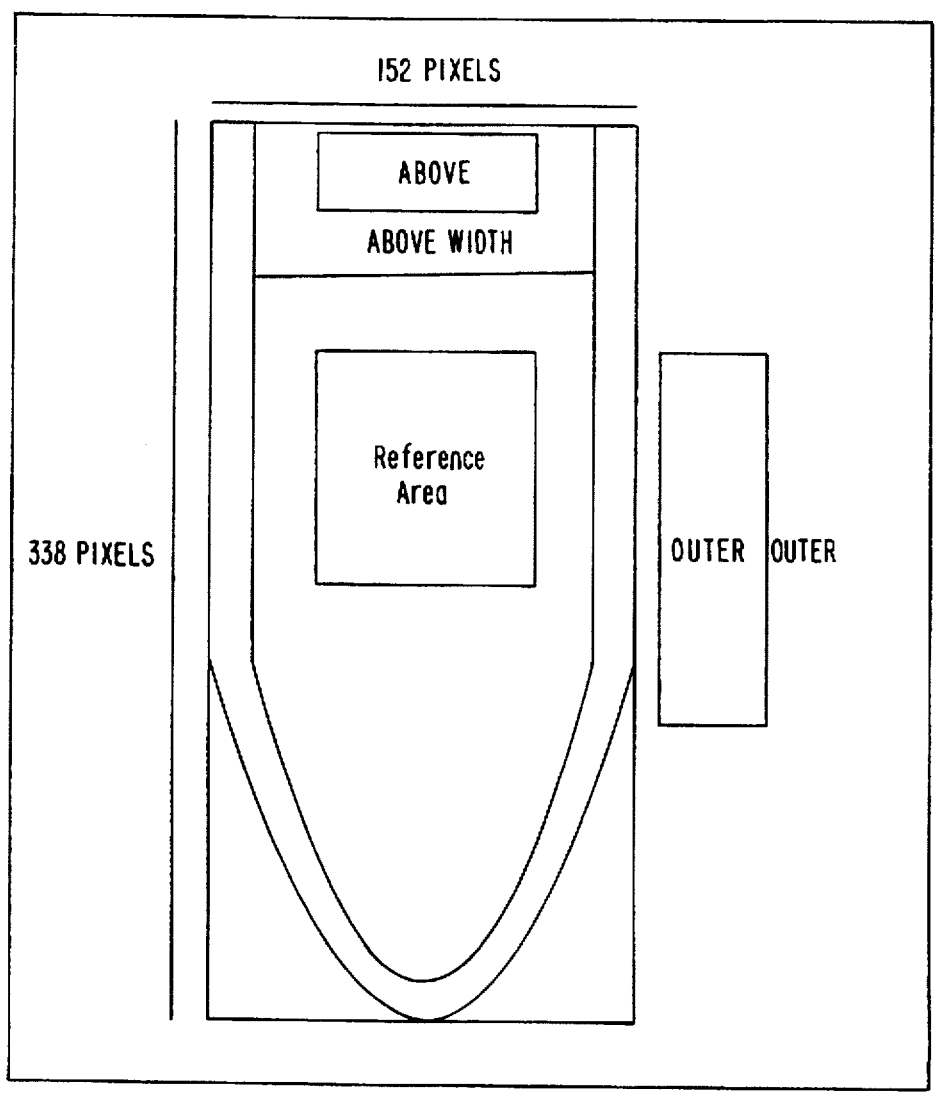
FIG. 15 shows various reference areas on the pixel array that are used to determine a set of reference values.

After the column detection program is completed, the feature calculation program begins. As an initial step in this program, various reference values are determined for subsequent use; and preferably, a respective set of such reference values is determined for each of the two columns illuminated on the pixel array. More particularly, the program selects three reference areas or regions for each column. As shown in FIG. 15, one region is located in the bead area inside the column, a second region is located above that bead area, and the third region is located outside the column.

After the desired reference areas are defined, the program determines values for the variable $R_{modus}$, $R_{max}$, $R_{min}$, $R_{outer}$ and $R_{above}$. In particular, $R_{modus}$ is set equal to the most frequent gray value in the reference region in the bead area inside the column. This reference value is a characteristic of the glass beads in column and is used as a threshold value in various subsequent processing steps. In addition, $R_{max}$ is set equal to the maximum gray value in the reference region in the bead area inside the column, and $R_{min}$ is set equal to the minimum gray value in that inside the column. $R_{outer}$ is set equal to the average gray value in the reference area outside the column, and $R_{above}$ is set equal to the average gray value in the reference area above the glass beads.

Next, the program begins to extract features related to the reaction that occurred in column 82. The features extracted include (1) parameters related to the cell pellet shape; (2) the red cell agglutinates in the column; and (3) the side to side balance of red cells in the column.

The cell pellet in the bottom of the column is first obtained by applying a global threshold in the V shape region of the column. The default threshold value is 54% of $R_{modus}$. In particular, the number of pixels in the V-shaped region of the column that have S values less than 54% of $R_{modus}$ is determined. The size of the pellet is calculated on the basis of the number of pixels inside the pellet area. If the size is larger than a given number, such as 200 pixels, the cell pellet is considered significant and the parameters related to the location of the cell pellet are determined. These parameters are illustrated in FIG. 16 and are defined as follows:

| Name | Description |
| --- | --- |
| leftx, lefty | left-most point in the upper border |
| rightx, righty | right-most point in the upper border |
| Ylimit | lowest y-coordinate in the upper border |
| pellety | bottom-most point in the bottom border |
| pelletx | gravity center of the part below Ylimit |

On the basis of these coordinates, the position of the window is readjusted by matching the center line of the window with pelletx.

To analyze the pellet shape, the upper border of the cell pellet is fitted with a linear line Y=a+bX. This line is determined as follows:

Assume the upper border of the pellet is defined by a set of points $$(x_i, y_i), i=1, N$$

where N=rightx=leftx−8 (The fitting does not includes the four points near the edge on each side). The error of the approximation line is defined as $$E = \sum_{i=1}^{N} (y_i^2 - Y_i^2)$$

To minimize this error, the coefficient a and b have to be $$b = \frac{NS_{xy} - S_x S_y}{NS_{xx} - S_x}$$

$$a = \frac{1}{N} S_y - b S_x$$

where $$S_x = \sum_{i=1}^{N} x_i \quad S_{xy} = \sum_{i=1}^{N} x_i y_i$$

$$S_y = \sum_{i=1}^{N} y_i \quad S_{xx} = \sum_{i=1}^{N} x_i^2$$

The residual of a pellet is calculated as $$\text{Residual} = \sqrt{\frac{\sum_{i=1}^{N} (y_i^2 - Y_i^2)}{N}}$$

On the basis of the above computation, three feature variable are obtained including the size of the cell pellet, the slope of the cell pellet, and the residual value. These variables are subsequently used to classify the agglutinate pattern.

Figure 17:
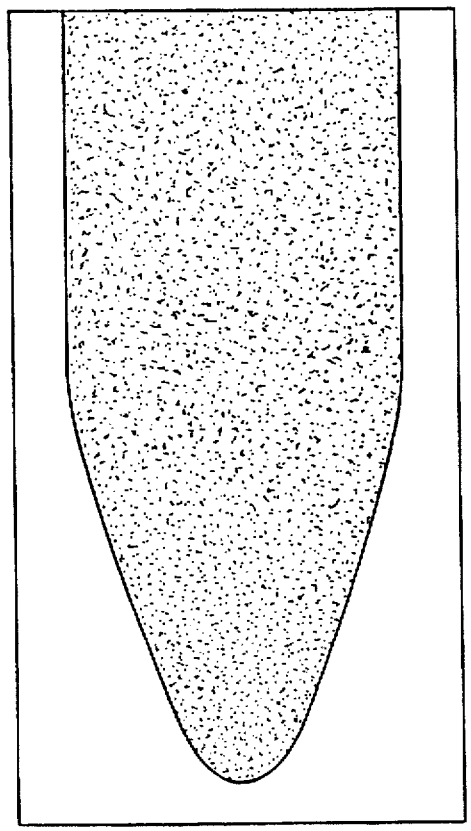
FIG. 17 shows a mask used in the image processing.

After these variables are obtained, a fixed mask, shown in FIG. 17, is used to cover the whole column area. This mask has the same width and shape as a column, and the mask is stored in a file and loaded into one memory frame on the Euresys board during image analysis. By matching the center and the bottom of the mask with those of the detected column, the mask is fitted onto the column.

Figure 18:
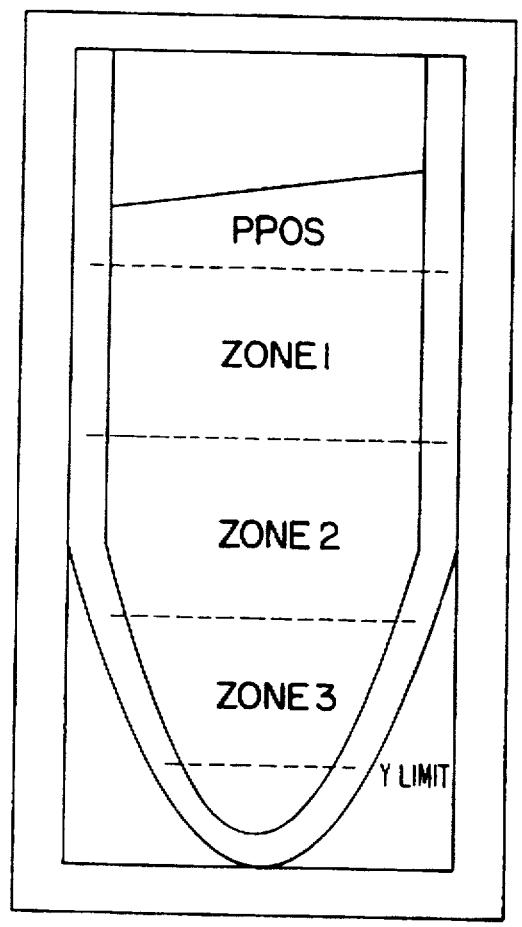
FIG. 18 illustrates the column separated into multiple zones.

The next step of the program is to extract the number of red cell agglutinates and their distribution in the column. For this purpose, the bead column is divided into five zones, shown in FIG. 18, referred to as the positive zone, the negative zone, and intermediate zones 1, 2, and 3. Generally, the positive zone is defined so as to contain the surface area on the top of the glass beads, and for example, it may be defined as the area above the line $Y_{top}$=80. The negative area is defined as the cell pellet area in the bottom of the column. If there is no cell pellet, then there is no negative area. The bead area between the positive and negative zones is divided into three areas of equal height to form the intermediate zones 1, 2, and 3. The size of the three intermediate zones is determined by $Y_{top}$ and $Y_{limit}$, and the height, H, of each zone is given by the equation:

$$H = \frac{Y_{limit} - Y_{top}}{3}$$

If there is no cell pellet and, thus, no negative area, then $Y_{limit}$ is defined as 40 pixels above the bottom of the column.

The next step in the program is to determine the number of pixels in the positive zone that are illuminated at an intensity below a given value, and for example, that given value may be 54% of $R_{modus}$. As discussed in greater detail below, the number of such pixels in the positive zone is used to determine if a strong positive reaction, such as a +4 reaction, occurred in the column.

Figure 19:
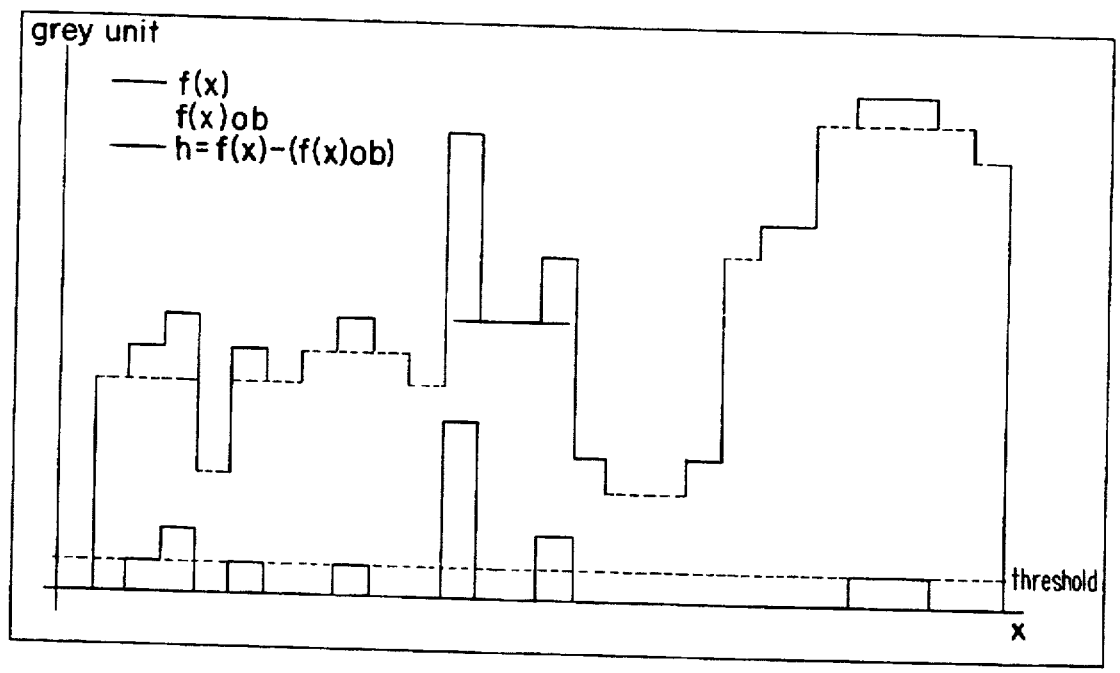
FIG. 19 illustrates the results of a top-hat transformation to a line slice of an image.

Then, the number of red cell agglutinates located in each of the intermediate zones is determined by means of an operation referred to as a top-hat operation and that finds the agglutinates on the basis of the local variation of the gray values. A top-hat operation is based on two basic operators: dilatation and erosion. The dilatation increases the size of an object and the erosion reduces the size of an object, and an erosion followed by a dilatation on an object is usually called as an opening operation. The top-hat transformation of an image, denoted h, is defined as:

$$h = f - (f \circ b)$$

where f is the input image and b is the structuring element function used by the opening (o). In the present application, the structuring element is kernel 7×7, and FIG. 19 shows an example of the top-hat transformation to a line slice of an image. After the dilation-erosion operation, a global cut-off is applied with a value equal to 12% of $R_{modus}$. The number of pixels in each intermediate zone having gray values, after the top-hat transformation, greater than 12% of $R_{modus}$ is determined. The parameters are then calculated by counting the number of pixels above the cutoff value in the zones 1, 2, and 3, and they correspond to the amount of red cell agglutinates in these zones.

Figure 20:
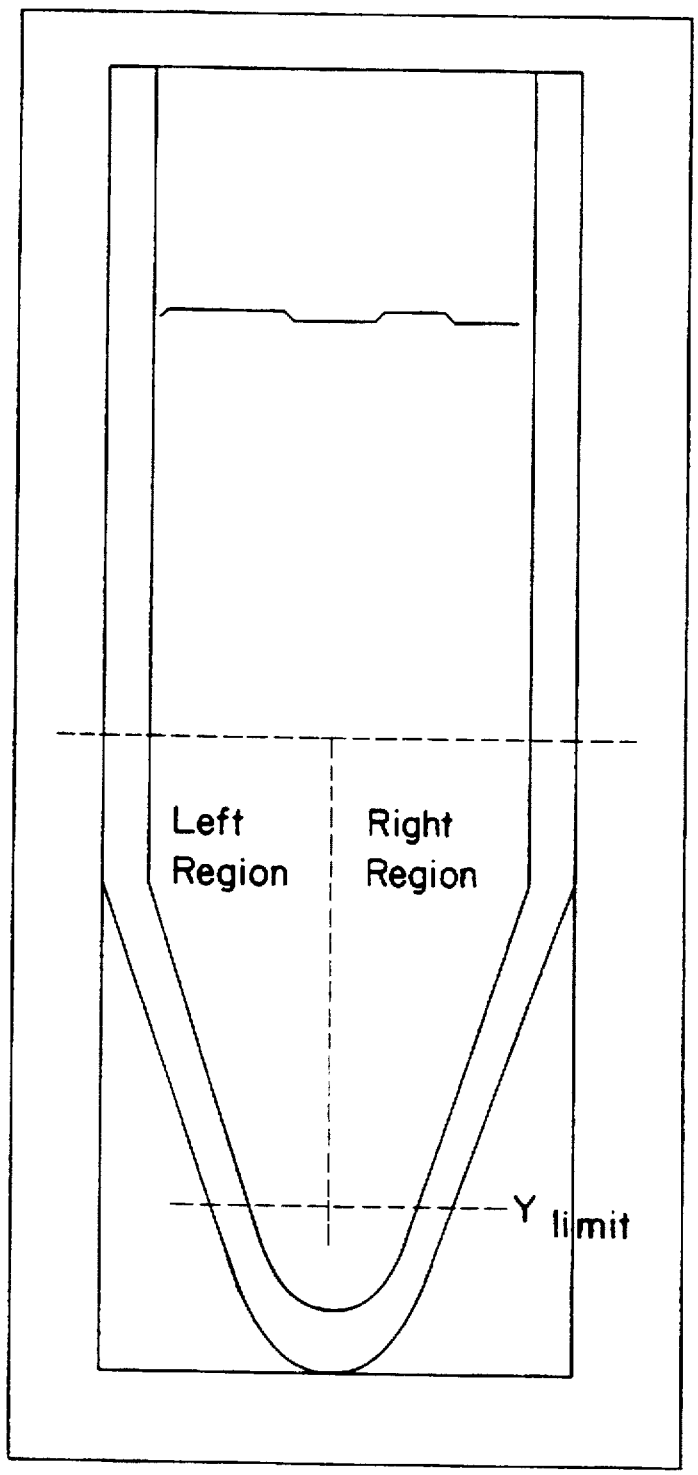
FIG. 20 shows the two parts of the column used to determine the balance of the red blood cell agglutinates in the column.

The feature calculation program then examines the balance of agglutinates between the left and right halves of the column, and in particular, between lower portions of the left and right halves of the column. The preferred area of the column that is used to determine that balance is shown in FIG. 20; and with reference thereto, that area extends upward for a given number of pixels, such as 120 pixels, from the lowest point ($Y_{limit}$) of the upper border of the cell pellet. The center line of the column is used to separate the area into two parts, as shown in FIG. 20. The number and location of red cells in the column and in the cell pellet were previously determined during the top-hat procedure and the global threshold, and this data are used to determine the number of red blood cells on the left and right sides of the column. The balance of agglutinate between the left and right halves of the column is considered as the difference between the numbers of red blood cells on the left and right sides of the column.

As discussed above, preferably two images, referred to as the front and back images, of each column are produced on the pixel array. The front image is produced, the column is then rotated 180°, and then the back image is produced. Preferably, values for each of the above-described parameters are obtained for each of the front and back images of the column, and then the two values for each parameter are summed.

Thus, the feature extraction program calculates the following features for each column: (1) the agglutinated red cells in the positive zone; (2) the cell agglutinates in intermediate zone 1, zone 2, and zone 3; (3) the size, slope, and residual of the cell pellet, and (4) the balance of the agglutinates between the left and right sides. These include a total of eight parameters.

Once values for the above-discussed parameters are obtained, the reaction grading program then uses these parameter to classify the reaction that occurred in the column into different classes. Generally, the program classifies the reaction as positive or negative; and if positive, as a class +1, +2, +3, or +4 reaction. In addition, the program is also capable of identifying a column as having an intermediate reaction, of identifying an empty cassette, and of indicating if a cassette cannot be read or if a column cannot be found.

The classifier is a linear decision tree on the basis of the Mahalanobis distance. This method is described in detail in the book "Methods Statistiques de Reconnaissance des Formes" by G. Gaillat (Ecole Nationale Superieure de Techniques Avancees). A simple mathematical definition of different calculations for the measurement of the separability between classes is given below.

Discriminate Analysis

Consider a set of N elements belonging to K classes. Each of the K subsets has $N_1, N_2, \ldots, N_K$ points, and is noted as $$X_k = \{x_{kn}\}$$

with $n = [1 \ldots N_k]$ and $k = [1 \ldots K]$ and element of subset (I, number of features).

The center of gravity of this subset is defined as $$\underline{X}_k = \frac{1}{N_k} \times \sum_{n=1}^{N_k} x_{kn}$$

and the covariance matrix as $$T_k = \sum_{n=1}^{N_k} (x_{kn} - \underline{X}_k)(x_{kn} - \underline{X}_k)^1$$

The center of gravity $\underline{X}$ and the covariance matrix T of the whole set are related to those of the subsets $\underline{X}_k$ and $T_k$ $$\underline{X} = \frac{1}{N} \times \sum_{k=1}^{K} N_k \times \underline{X}_k$$

$$T = \sum_{k=1}^{K} T_k + \sum_{k=1}^{K} N_k(\underline{X}_k - \underline{X})(\underline{X}_k - \underline{X})^1$$

Now we define $$V = \sum_{k=1}^{K} T_k.$$

which is the sum of Covariance matrixes of different classes, termed as the intraclass covariance matrix, and $$W = \sum_{k=1}^{K} N_k(\underline{X}_k - \underline{X})(\underline{X}_k - \underline{X})^1$$

which is the covariance matrix of a set constituted by K points $\underline{X}_k$ with coefficients $N_k$, termed as the interclass covariance matrix.

Accordingly we define two additional terms the intraclass variance, v, and the interclass variance, w, as follows:

$$v = \text{trace}(V) = \sum_{k=1}^{K} \sum_{n=1}^{N_k} \|X_{kn} - \underline{X}_k\|^2$$

which measures how the elements belonging to one class are grouped around their center of gravity. The smaller it is, the nearer the elements are to the center of gravity. If the intraclass variance was equal to 0, the elements of a class would be concentrated on their center of gravity. The interclass variance, w, is defined as follows:

$$w = \text{trace}(W) = \sum_{k=1}^{K} \|\underline{X}_k - \underline{X}\|^2$$

which is the dispersion between classes. The greater it is, the more classes are separated from each other. If all centers of gravity aggregated to their center $\underline{X}$, then the interclass variance would be equal to 0.

In pattern recognition, the ratio w/v can be used as a measure of separability between classes. If it is great, then classes form compact sets and are all separated from each other. In contrast, if this ratio is small, it will be difficult to distinguish classes.

The purpose of discriminate analysis is to project a set of data into a J-dimensional sub-space in a way that the different classes are most separated. This corresponds to maximize the ratio of the interclass variance w over the interclass variance v to be maximum in the sub-space.

If the data set is projected into a one-dimensional space with a unitary vector u, then the intraclass and interclass variances of the projected set can be calculated $$v_u = u^t V u$$

$$w_u = u^t W u$$

where V is the interclass covariance matrix and W is the intraclass covariance matrix. Consider the ratio $$r_u = \frac{W_u}{V_u}.$$

The maximum of this ratio can be found when the gradient $$\text{grad}(r_u) = \frac{1}{v_u^2} \times (v_u \text{grad}(w_u) - w_u \text{grad}(v_u))$$

becomes zero. That is, the vector $\text{grad}(v_u)$ and $\text{grad}(w_u)$ are co-linear:

$$\text{grad}(W_u) = \lambda \text{grad}(V_u)$$

or $$Wu = \lambda Vu$$

where $\lambda$ is a parameter. If V can be inverted, then $$V^{-1} Wu = \lambda u$$

This equation shows that the ratio $r_u$ is maximum when the direction of the projection axis is defined by the eigenvector associated to the highest eigenvalue of matrix $V^{-1} W$. This can also be demonstrated to be true for the J-dimensional sub-space.

To separate the data into various classes, the feature data is first projected into a sub-dimensioned space to maximize the separability of the data. A classifier has been developed to separate the data in the sub-dimensional space.

Mahalanobis Distance

If a data set consists of K classes $(w_1, w_2, \ldots, W_k)$ and has Gaussian distribution, then for each point X, the probability of X belonging to class $W_k$ can be written as $$f_{wk}(X) = p(w_k) \cdot f(X|w_k)$$

with $f_{wk}(X)$ is a probability of X belonging to $W_k$; $p(w_k)$ is the probability of $w_k$ in the whole data set; $f(X|w_k)$ is a conditional probability of X given that it belongs to $w_k$. The classical Bayesian approach for pattern recognition is to select a class that maximizes $f_{wk}(X)$.

When the samples obey the Gaussian distribution, the above approach is equivalent to search the maximum of $$g_k(X) = -(X - \underline{X}_k)' T_k^{-1} (X - \underline{X}_k) + [\log (\det(T_k)) - 2\log(p(w_k))]$$

The first term can be interpreted as a square of a distance between X and the center $X_k$, called a Mahalanobis distance. The second term is a correction term dependent on class k but not on X. A set of surfaces defined by $$(X - \underline{X}_k)' T_k^{-1} (X - \underline{X}_k) = \text{constant}$$

constitutes a group of concentric ellipsoids, with center $\underline{X}_k$.

In the case that the projection space is two-dimensional, the function $g_k(X)$ can be written explicitly. The calculation is simplified by suppressing the corrective term if the equiprobability of the classes is considered.

Assume the sample X is represented by the coordinates (x,y), the center of gravity of class k is $(x_k, y_k)$, and the inverse of the covariance matrix of class, $kT_k^{-1}$, is $$\begin{bmatrix} T_{k,11} & T_{k,12} \\ T_{k,21} & T_{k,22} \end{bmatrix}$$

which is symmetric $T_{k,12} = T_{k,21}$. Thus, assume $G_k(x,y) = -g_k(X)$ and it can be written as $G_k(x,y) = T_{k,11}(x-x_k)^2 + 2 \times T_{k,12}(x-x_k)(y-y_k) + T_{k,22}(y-y_k)^2$ $G_k(x,y)$ is a second degree polynomial, and we want to find the minimum $G_k$.

Classifier

The samples are graded into different classes on the basis of a linear decision tree. This program classifier first separates the samples into two principal groups. One group, Group I, contains the classes +1, +2, +3, and +4 reactions, and the other group, Group II, includes 0 and very weak positive reactions. The classifier identifies these following classes:

| Class | Description |
|---|---|
| 0 | Negative reaction |
| 1 | Positive reaction |
| 2 | Posiive reaction |
| 3 | Positive reaction |
| 4 | Strong positive reaction |
| -2 | Can't read cassette or column not found |

-continued

| Class | Description |
|---|---|
| -4 | Intermediate reaction |
| -5 | Empty cassette |

Figure 21:
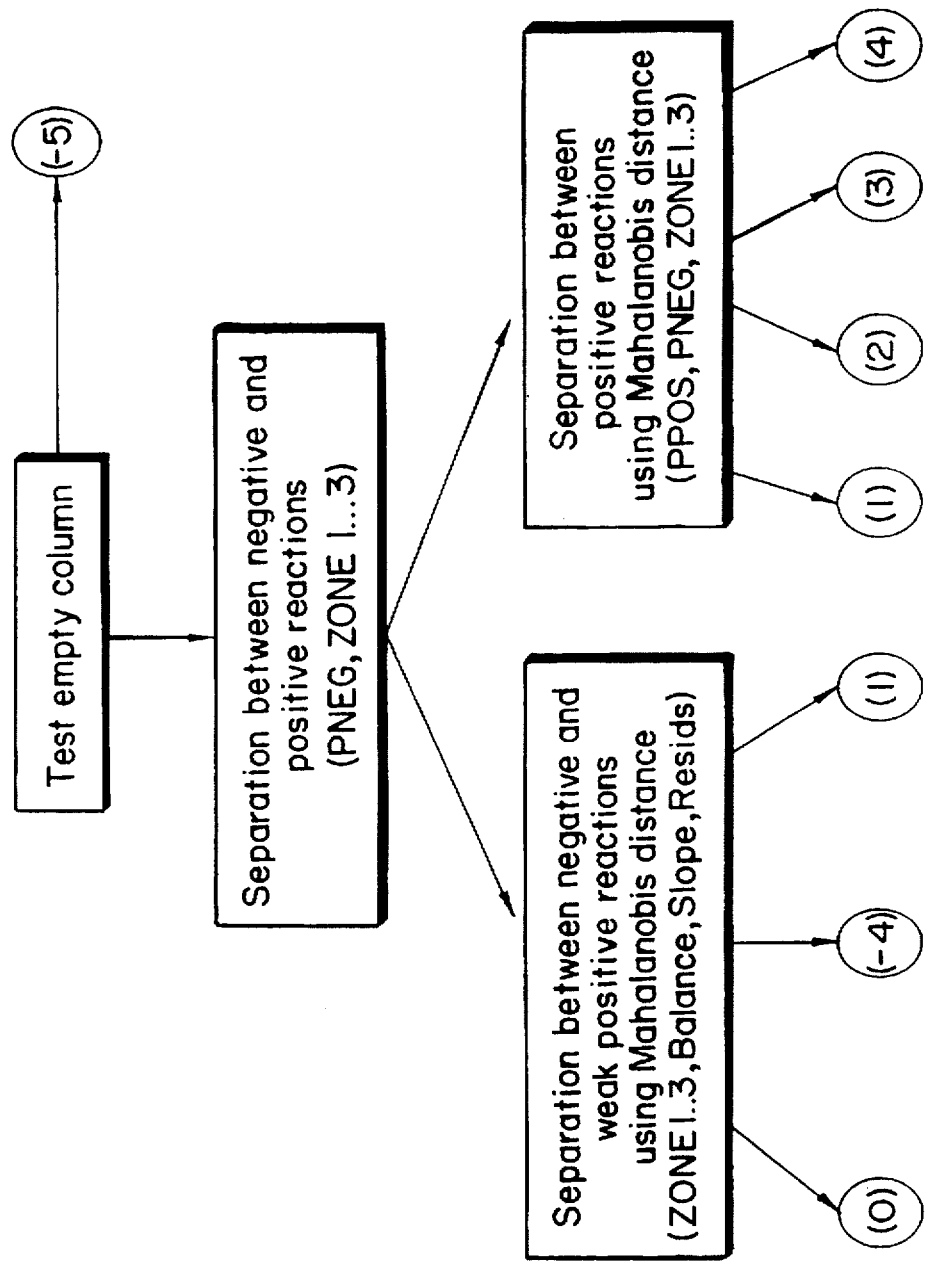
FIG. 21 is a different version of the Decision Tree.

FIG. 21 shows a flow chart summarizing the global structure of the classifier. The feature data used in each decision are shown in the Figure and are detailed as follows:

Empty Column

To determine if a column is empty, the total red cells in a whole column, including the negative zone, positive zone, and three intermediate zones, are summarized. If the value is less than a given number such as 500, the column is graded as an empty column. That is Sum_whole=PPos+PNeg+Zone1+Zone2+Zone3 if (Sum_whole<500), then (empty column)

Separation into two groups

The negative class reactions are separated from the majority of the positive class reactions on the basis of the size of the cell pellet and the sum of the agglutinates in zones 1, 2, and 3. That is:

if (PNeg<500) or (Sum_Zones>800), then positive reaction {1, 2, 3, 4} else negative reaction {0,1}

Classification of {1,2,3,4}

The positive reactions are further separated into class +1, +2, +3, and +4 reactions on the basis of the distribution of agglutinates in the column. The distribution of the agglutinates is represented by the five features: PPos, Zone1, Zone2, Zone3, and PNeg. Table 1 lists the average feature data of four types of positive reactions. The results indicate how the feature data vary among positive reactions.

TABLE 1

Average feature data of different reaction classes.

| Features | Class 1 | Class 2 | Class 3 | Class 4 |
|---|---|---|---|---|
| PPos | 22 | 304 | 2183 | 3860 |
| Zone 1 | 358 | 1238 | 1745 | 259 |
| Zone 2 | 362 | 1034 | 700 | 43 |
| Zone 3 | 359 | 786 | 270 | 58 |
| PNeg | 2065 | 764 | 26 | 19 |
| Number of samples | 281 | 328 | 173 | 45 |

The classification is done by Mahalanobis distance, which is able to separate correctly the different types of reactions.

Classification of {0,1}

The separation of these two classes uses the following features: (i) the sum of agglutinates in zones 1, 2, and 3, (ii) the slope and (iii) the residuals of the cell pellet upper border, and (iv) the side to side balance of red cells. In order to increase the separability between the two classes, the discriminate analysis is applied. The above four features are projected into one dimension space. The variation of the separability is significant. Before the projection, the separability is equal to 0.70 and after projection, 1.38. This means that the elements of each class are more regrouped around their center of gravity and the distance between the two classes is increased. The projection is calculated as following:

Projection=0.78×Aqglutinates+0.48×residuals+0.36×slope+0.13×balance

The coefficients are calculated by discriminate analysis. They show the importance of each feature for the projection.

The limit between classes is estimated by Mahalanobis distance. The result may also include an indeterminate class. It may be defined by the difference between the two Mahalanobis distances calculated for both classes. If the absolute difference is below 1.2, then the sample is classified as a questionable reaction. This third class is on the boundary between classes 0 and 1.

While it is apparent that the invention herein disclosed is well calculated to fulfill the objects previously stated, it will be appreciated that numerous modifications and embodiments may be devised by those skilled in the art, and it is intended that the appended claims cover all such modifications and embodiments as fall within the true spirit and scope of the present invention.

What is claimed is:

1. A method for analyzing a solution for an agglutination pattern, comprising:

producing an illuminated image of the solution on an array of pixels;

assigning to each pixel in the array and on said illuminated image, a data value representing an intensity of the illumination of the pixel; and processing the data values to determine values for a predefined set of variables to determine if an agglutination pattern is present in the solution; and if an agglutination pattern is present, classifying the agglutination pattern into one of a plurality of predefined classes;

wherein, if an agglutination pattern is present in the solution, the determined values for the predefined set of variables identify a distribution of agglutinates in the solution; and the classifying step includes the step of classifying the agglutination pattern into one of the plurality of predefined classes on the basis of said distribution.

2. A method according to claim 1, wherein the processing step includes the steps of:

separating the array of pixels into a plurality of zones;

processing the data values for the pixels in each zone according to a respective predetermined procedure to determine values for a predefined set of variables; and processing said determined values to determine whether an agglutination pattern is present and, if an agglutination pattern is present, to classify the pattern into one of the predefined classes.

3. A method according to claim 2, wherein the solution is in a column having a bottom, a lower portion, and a filter disposed in said lower portion, and wherein the separating step includes the steps of:

identifying a first zone of pixels adjacent a top of the filter; and identifying a second zone of pixels adjacent the bottom of the column.

4. A method according to claim 3, wherein the step of processing the data values to determine values for the predefined set of variables includes the steps of:

assigning to a first variable a value representing the number of pixels in the first zone having a data value less than a first value;

assigning to a second variable a value representing the number of pixels in the second zone having a data value less than a second value.

5. A method according to claim 4, wherein the step of processing the data values to determine values for the predefined set of variables further includes the step of establishing a reference value;

the step of assigning a value to the first variable includes the step of assigning to the first variable a value representing the number of pixels in the first zone having a data value less than a given percentage of the reference value; and the step of assigning a value to the second variable includes the step of assigning to the second variable a value representing the number of pixels in the second zone having a data value less than a given percentage of the reference value.

6. A method according to claim 5, wherein the establishing step includes the steps of:

defining a reference area on the pixel array;

establishing as the reference value, the most common data value for the pixels in the reference area.

7. A method according to claim 6, wherein the defining step includes the step of defining the reference area in the image of the column on the pixel array.

8. A method according to claim 7, wherein the step of defining the reference area in the image of the column further includes the step of defining the reference area in the image of the filter on the pixel array.

9. A method according to claim 4, wherein the separating step further includes the step of identifying a plurality of additional zones of pixels between said first and second zones.

10. A method according to claim 9, wherein the step of processing the data values to determine values for the predefined set of variables further includes the step of assigning to an additional set of variables values representing the numbers of pixels in the additional zones having data values less than a third value.

11. A method according to claim 1, wherein the assigning step includes the step of identifying the pixels on the array and in the illuminated image of the solution.

12. A method according to claim 11, wherein the illuminated image has left and right edges, and the identifying step includes the step of identifying the pixels on the left and right edges of the illuminated image.

13. A method according to claim 2, wherein the solution is in a column having a bottom, and wherein:

the step of processing the data values for the pixels include the step of processing the data values to determine if a pellet of cells is located in the bottom of the column; and the predefined set of variables include the size of the pellet, and the slope and shape of a top surface of the pellet.

14. A method according to claim 13, wherein the column includes left and right halves, and each of said halves includes a number of blood cells, and wherein the predefined set of variables further includes the difference between the numbers of blood cells on the left and right halves of the column.

15. A method for analyzing a solution for an agglutination pattern, comprising:

producing an illuminated image of the solution on an array of pixels;

assigning to each pixel on the illuminated image, a data value representing the intensity of the illuminated image on the pixel;

separating the array of pixels into a plurality of zones; and processing the data values of the pixels in each region according to a predetermined program to determine values for a predefined set of variables to determine whether an agglutination pattern is present in the solutions;

wherein, if an agglutination pattern is present in the solution, the determined values for the predefined set of variables identify a distribution of agglutinates in the solution.

16. A method according to claim 15, further including the step of, if an agglutination pattern is present in the solution, classifying the agglutination pattern into one of a plurality of predefined classes.

17. A method according to claim 16, wherein the processing step includes the steps of:

processing the data values for the pixels in each zone according to a respective predetermined procedure to determine values for a predefined set of variables; and processing said determined values to determine whether an agglutination pattern is present.

18. A method according to claim 1, wherein the solution is in a container having a bar code identifying data, and further comprising:

reading the bar code on the cassette; and omitting the processing step if the bar code does not identify all of preselected data.

19. A method according to claim 1, wherein the solution is in a container, and further comprising:

if the container has preselected alignment marks, positioning the container to locate the alignment marks in preset positions to align the container with the pixel array, and omitting the processing step if the alignment marks are not located in the preset positions; and if the container does not have preselected alignment marks, omitting the processing step.

20. A system for analyzing a solution for an agglutination pattern, comprising:

means for holding the solution;

a pixel array;

illumination means for producing an illuminated image of the solution on the pixel array;

means to assign to each pixel on the illuminated image, a data value representing the intensity of the illuminated image on the pixel; and processing means to process said data values according to a predetermined program wherein the processing means includes means to separate the array of pixels into a plurality of zones; means to process the data values for the pixels in each zone according to a respective predetermined procedure to determine values for a predefined set of variables; and means to use said determined values to determine whether an agglutination pattern is present in the solution in the sample container; and if an agglutination pattern is present, to classify the agglutination pattern into one of a plurality of predefined classes;

wherein, if an agglutination pattern is present in the solution, the determined values for the predefined set of variables identify a distribution of agglutinates in the solution, and the means to classify the agglutination pattern includes means to classify the agglutination pattern based on said distribution.

21. A system according to claim 20, wherein the holding means includes a base;

a frame for holding the solution and pivotally connected to the base;

moving means connected to the frame to pivot the frame and the solution to position first and second opposite sides of the solution facing the pixel array.

22. A system according to claim 21, wherein the solution is contained within a cassette, and the frame forms an elongated channel for holding the cassette.

23. A system according to claim 22, wherein the elongated channel includes first and second opposite, open ends to allow sliding movement of the cassette into, through and from the elongated channel.

24. A system according to claim 23, further comprising a storage rack located adjacent the frame, and forming a multitude of elongated channels for holding a multitude cassettes; and indexing means connected to the storage rack to move the storage rack through a series of positions to align each of the elongated channels of the storage rack with the elongated channel of the frame.

25. A system according to claim 24, wherein the cassettes includes bar codes identifying the cassettes, and the system further includes a code reader for reading the bar code and identifying the cassettes.

26. A system according to claim 21, wherein the cassettes include at least one positioning mark, and further comprising means to locate the cassettes in the frame with the positioning marks in predetermined locations.

27. A system according to claim 20, wherein the processing means includes:

means to separate the array of pixels into a plurality of zones;

means to process the data values for the pixels in each zone according to a respective predetermined procedure to determine values for a predefined set of variables; and means to process said determined values to determine whether an agglutination pattern is present, and if an agglutination pattern is present, to classify the pattern into one of the predefined classes.

28. A system according to claim 27, wherein the solution is in a column having a bottom, a lower portion, and a filter disposed in said lower portion, and wherein the means to separate the array of pixels includes means to identify a first zone of pixels adjacent a top of the filter, and to identify a second zone of pixels adjacent the bottom of the column.

29. A system according to claim 28, wherein the processing means further includes means to define a reference area on the pixel array; and means to establish as a reference value, the most common data value for the pixels in the reference area.

30. A system according to claim 20, wherein the means to assign a data value to each pixel includes means to identify the pixels on the array and in the illuminated image of the solution.

* * * * *

UNITED STATES PATENT AND TRADEMARK OFFICE
CERTIFICATE OF CORRECTION

PATENT NO. : 5,768,407
DATED : June 16, 1998
INVENTOR(S) : Jian Shen et al.

It is certified that error appears in the above-identified patent and that said Letters Patent is hereby corrected as shown below:

Column 21, Lines 4 - 5, delete "solutions;" and insert therefor --solution;--.

Signed and Sealed this

First Day of December, 1998

Attest:

BRUCE LEHMAN

*Attesting Officer*     *Commissioner of Patents and Trademarks*